US012582610B2

(12) United States Patent
Shah et al.

(10) Patent No.: US 12,582,610 B2
(45) Date of Patent: Mar. 24, 2026

(54) LIPID-POLYMER COMPOSITIONS AND METHODS OF USE

(71) Applicant: Max Biology Co. Ltd., Phnom Penh (KH)

(72) Inventors: Sunil Shah, Birmingham (GB); Sean Ngu, Phnom Penh (KH); Afzal R. Mohammed, Birmingham (GB)

(73) Assignee: Max Biology Co. Ltd., Phnom Penh (KH)

( * ) Notice: Subject to any disclaimer, the term of this patent is extended or adjusted under 35 U.S.C. 154(b) by 0 days.

(21) Appl. No.: 18/223,187

(22) Filed: Jul. 18, 2023

(65) Prior Publication Data

US 2023/0355539 A1 Nov. 9, 2023

Related U.S. Application Data

(62) Division of application No. 17/323,052, filed on May 18, 2021.

(60) Provisional application No. 63/026,306, filed on May 18, 2020.

(51) Int. Cl.

| | |
|---|---|
| ***A61K 9/51*** | (2006.01) |
| ***A61K 9/00*** | (2006.01) |
| ***A61K 45/06*** | (2006.01) |
| *B82Y 5/00* | (2011.01) |

(52) U.S. Cl.

CPC .......... *A61K 9/5123* (2013.01); *A61K 9/0048* (2013.01); *A61K 9/5146* (2013.01); *A61K 9/5192* (2013.01); *A61K 45/06* (2013.01); *B82Y 5/00* (2013.01)

(58) Field of Classification Search

CPC ...... B82Y 5/00; A61K 9/5123; A61K 9/0048; A61K 9/5146; A61K 9/5192; A61K 45/06

See application file for complete search history.

(56) References Cited

U.S. PATENT DOCUMENTS

| | | | |
|---|---|---|---|
| 6,482,517 B1 | 11/2002 | Anderson | |
| 6,964,778 B1 | 11/2005 | Hui et al. | |
| 8,226,968 B2 | 7/2012 | Gaal et al. | |
| 2012/0270953 A1 | 10/2012 | Gilbard et al. | |
| 2012/0328702 A1* | 12/2012 | Edelson | A61P 19/02 424/490 |
| 2019/0216869 A1 | 7/2019 | Salm et al. | |
| 2019/0216870 A1 | 7/2019 | Witowski et al. | |
| 2019/0314296 A1 | 10/2019 | Wright et al. | |
| 2020/0078427 A1 | 3/2020 | Rhodes et al. | |
| 2020/0375918 A1 | 12/2020 | Rubinov et al. | |
| 2021/0353554 A1 | 11/2021 | Shah et al. | |
| 2023/0405025 A1 | 12/2023 | Shah et al. | |

FOREIGN PATENT DOCUMENTS

| | | | | |
|---|---|---|---|---|
| CA | 2929280 | A1 | 5/2015 | |
| CA | 3089686 | A1 | 9/2016 | |
| CN | 101579312 | A | 11/2009 | |
| CN | 101732349 | A | 6/2010 | |
| CN | 108434101 | A | 8/2018 | |
| CN | 110251466 | A | 9/2019 | |
| EP | 3424494 | A1 | 1/2019 | |
| EP | 3478266 | A1 | 5/2019 | |
| WO | WO-1994/026252 | A1 | 11/1994 | |
| WO | WO-9711682 | A2 * | 4/1997 | A61K 9/1075 |
| WO | WO-2014/078470 | A1 | 5/2014 | |
| WO | WO-2014/100231 | A1 | 6/2014 | |
| WO | WO-2015168523 | A1 * | 11/2015 | A61K 31/4709 |
| WO | WO-2018/002636 | A1 | 1/2018 | |
| WO | WO-2018/060282 | A1 | 4/2018 | |
| WO | WO-2020/077103 | A1 | 4/2020 | |
| WO | WO-2021/234548 | A1 | 11/2021 | |
| WO | WO-2022/074541 | A1 | 4/2022 | |

OTHER PUBLICATIONS

Andrew Bodratti & Paschalis Alexandridis, Formulation of Poloxamers for Drug Delivery, 9 J Funct. Biomater. 11 (Year: 2018).*

Roonal Jain & J.P. Shastri, Study of Ocular Drug Delivery System Using Drug-Loaded Liposomes, 1 Intl. J Pharm. Invest. 35 (Year: 2011).*

U.S. Appl. No. 18/030,439, Shah et al.

International Search Report and Written Opinion for International Application No. PCT/IB2021/054231, mailed Aug. 4, 2021 (14 pages).

International Search Report and Written Opinion for PCT/IB2021/059094, mailed Mar. 3, 2022 (20 pages).

Xiaohong et al., "Mechanism of surfactant micelle formation," Langmuir. 24(19):10771-5 (Oct. 2008).

Bondok et al., "Adverse Ocular Impact and Emerging Therapeutic Potential of Cannabis and Cannabinoids: A Narrative Review", Clinical Ophthalmology 2024:18 3529-3556 (Nov. 2024).

Minnelli et al., "A Poloxamer-407 modified liposome encapsulating epigallocatechin-3-gallate in the presence of magnesium: Characterization and protective effect against oxidative damage," Int J Pharma. 552;225-234 (Dec. 2018).

* cited by examiner

*Primary Examiner* — Sean M Basquill

(74) *Attorney, Agent, or Firm* — Clark & Elbing LLP

(57) ABSTRACT

The present invention features new lipid-polymer composite particles that are useful for the formulation of bioactive agents for administration to a subject. The nanoparticles include a block copolymer, a lipid, e.g., phospholipid, and a sterol. The formulations of a bioactive agent (e.g., a therapeutic agent, a nutraceutical agent, or a recreational agent) described herein provide for easier loading of lipid-polymer composite particles with higher drug loading capacity, increased stability of the formulations, and lower surface tension of water, which allows for lipid coating and entrapment.

14 Claims, 25 Drawing Sheets

| | | Effective Diameter | | Polydispersity | |
|---|---|---|---|---|---|
| | | Mean | S.D. | Mean | S.D. |
| 0.02% CBD | Fc1 | 169.50 | 51.39 | 4.93 | 4.30 |
| | Fc2 | 122.75 | 10.41 | 0.07 | 0.07 |
| | Fc9 | 125.22 | 6.91 | 0.24 | 0.15 |
| 0.25% CBD | Fc3 | 141.27 | 37.80 | 0.56 | 0.36 |
| | Fc4 | 83.94 | 12.14 | 0.49 | 0.47 |
| | Fc5 | 101.36 | 7.53 | 0.25 | 0.16 |
| | Fc6 | 113.57 | 15.47 | 0.06 | 0.03 |
| | Fc8 | 135.45 | 12.83 | 0.42 | 0.37 |
| | Fc7 | 317.45 | 31.87 | 0.34 | 0.03 |

FIG. 3

| | Zeta Size | |
|---|---|---|
| | Mean | S.D. |
| Fc1 | -24.79 | 4.30 |
| Fc2 | -26.05 | 5.29 |
| Fc9 | -30.07 | 2.35 |
| Fc3 | 0.00 | 0.00 |
| Fc4 | -0.05 | 0.09 |
| Fc5 | 0.00 | 0.00 |
| Fc6 | -38.08 | 5.66 |
| Fc8 | -7.93 | 13.59 |
| Fc7 | -25.77 | 5.16 |

FIG. 4

Concentration of F127: 1% 2% 3% 4% 5% 10%

Concentration of CBD: 0.5%

| | Formulation | Freezing point | mOsm |
|---|---|---|---|
| | Saline | -0.5 | 342.23 |
| | 1% F127 +0.5 %CBD | -0.1 | 104.57 |
| | 3% F127 +0.5 %CBD | -0.3 | 223.40 |
| | 5% F127 +0.5 %CBD | -0.1 | 104.57 |
| 0.5% CBD and lipids added via ethanol injection to homogenised F127 | Fe1 | -0.5 | 342.23 |
| | Fe4 | -0.5 | 342.23 |
| | Fe7 | -0.7 | 461.06 |
| lipids added via ethanol injection to homogenised F127 + 0.5% CBD | Fe2 | -0.6 | 401.65 |
| | Fe5 | -0.5 | 342.23 |
| | Fe8 | -0.7 | 461.06 |
| lipids added directly to homogenised F127 + 0.5% CBD | Fe3 | Na | Na |
| | Fe6 | Na | Na |
| | Fe9 | Na | Na |
| | Hyabak® 0.15% | -0.6 | 401.65 |
| | Thealoz® Duo New | -0.4 | 282.82 |
| | Thealoz® Duo | -0.7 | 461.06 |

FIG. 14

5% Pluronic F127

DSPC:Chol
(0.21:0.19 mM)

5% Pluronic F127
+ DSPC:Chol
(0.21:0.19 mM)

LIPID-POLYMER COMPOSITIONS AND METHODS OF USE

BACKGROUND OF THE INVENTION

Delivery of bioactive agents with low solubility in aqueous media has been a challenge for drug delivery. An approach for targeted delivery of insoluble bioactive agents has been the use of liposomes and/or micellar nanoparticles as carrier systems. Challenges with stability, degradation, and bioavailability have, however, hindered the widespread implementation of such delivery systems. Accordingly, new formulations of nanoparticle delivery systems are required for effective delivery of bioactive agents.

SUMMARY OF THE INVENTION

In one aspect, the invention provides a composition that includes a plurality of lipid-polymer composite particles encapsulating a bioactive agent. The lipid-polymer composite particles may include a block copolymer, a lipid (e.g., a neutral lipid, a cationic lipid, or an anionic lipid), and a sterol. The plurality of lipid-polymer composite particles may have a mean particle size of from about 10 nm to about 1000 nm (e.g., from about 10 nm to about 500 nm, from about 10 nm to about 100 nm, from about 500 nm to about 1000 nm).

In some embodiments, the bioactive agent is a therapeutic agent, a nutraceutical agent, or a recreational agent.

In some embodiments, the bioactive agent is a cannabinoid or a cannabinoid derivative, a terpene, a flavonoid, an antibiotic, an antiseptic agent, an antifungal, an antibacterial, an analgesic, an anti-inflammatory agent, an antiprotozoal agent, a steroid, an antiviral agent, a lipophilic drug, an anti-VEGF agent, an anti-glaucoma agent, an essential oil, an immunogen (e.g., a vaccine component), nicotine or a nicotine analogue, cyclosporin A, tacrolimus, isotretinoin, propofol, griseofulvin or any combination thereof. In some embodiments, the essential oil comprises tea tree oil, myrrh oil, eucalyptus oil, clove oil, lavender oil, peppermint oil, Roman chamomile oil, German chamomile oil, frankincense oil, helichrysum oil, cypress oil, angelica oil, labdanum oil, petitgrain bigarade oil, orange bigarade oil, bergamot oil, sweet orange oil, palmarosa oil, lemon-scented ironbark oil, may chang oil, basil oil, sweet marjoram oil, geranium oil, patchouli oil, valerian oil, sandalwood oil, neroli bigarade oil, grapefruit oil, coriander oil, citronella oil, black peppermint oil, gully gum oil, juniper twig oil, spearmint oil, scots pine oil, rosemary oil, clary oil, ginger oil, lemon oil, mandarin oil, cumin oil, juniper berry oil, lemon balm oil, myrtle oil, Ravensara oil, sweet thyme oil, everlasting oil, manuka oil, dwarf pine oil, oregano oil, vetiver oil, Melissa oil, white fir oil, cassia oil, lemongrass oil, lime oil, wintergreen oil, fennel oil, ylang ylang oil, or a combination thereof. In some embodiments, the concentration of the essential oil is from 0.01% to 95% 35 by weight (e.g., 5%, 10%, 15%, 20%, 25%, 30%, 35%, 40%, 45%, 50%, 55%, 60%, 65%, 70%, 75%, 80%, 85%, 90%, or 95%) of the composition. In some embodiments, the composition includes a plurality of essential oils. In some embodiments, the plurality of essential oils comprises from 2 to 10 essential oils. In some embodiments, the concentration of the plurality of essential oils is from 0.01% to 95% by weight (e.g., 5%, 10%, 15%, 20%, 25%, 30%, 35%, 40%, 45%, 50%, 55%, 60%, 65%, 70%, 75%, 80%, 85%, 90%, or 95%) of the composition. In some embodiments, the composition is formulated as an eye drop formulation.

In some embodiments, the block copolymer is a poloxamer (e.g., poloxamer 407).

In some embodiments, the weight ratio of the poloxamer and the bioactive agent is from about 2 to about 15.

In some embodiments, the lipid includes a carbon chain of length from 4 to 22 and a head group having a neutral, or cationic, or anionic head group. In some embodiments, the lipid is a phosphatidylcholine, a phosphatidylserine, a phosphatidylglycerol, a phosphatidylethanolamine, or a phosphatidylinositol.

In some embodiments, the concentration of the lipid is from about 0.1 mol % to about 10 mol %. In some embodiments, the sterol is a phytosterol, a synthetic sterol, cholesterol, or a cholesterol analog.

In some embodiments, the concentration of the sterol is form about 5 mol % to about 50 mol % of the total lipid composition.

In some embodiments, the weight ratio of the sterol to the lipid is from about 0.01 to about 0.50.

In another aspect, the invention features an immunogenic composition comprising a composition as described herein.

In another aspect, the invention features a method of providing a bioactive agent to a subject by administering the composition of any of the above embodiments to the subject.

In some embodiments, the bioactive agent includes a cannabinoid and the dose is from about 0.01 mg/kg to about 30 mg/kg.

In some embodiments, mode of administration is topical, orally, by injection, sublingually, buccally, rectally, vaginally, by ocular route, by otic route, by nasal route, by inhalation, by nebulization, or transdermally.

In another aspect, the invention features a method of preparing the composition of any of the above embodiments. In some embodiments, preparation of the composition of any of the above embodiments includes a multi-step process. In some embodiments, the multi-step process includes a first step including homogenization of the bioactive agent with the polymer of any of the above embodiments to produce a homogenized solution and a second step including injection (e.g., immersed injection) of the lipid and the sterol of any of the above embodiments into the homogenized solution of the first step.

In another aspect, the invention provides a method of treating dry eye disease, inflammation, eye pain, pink eye, dark eye circles, red eye, bacterial eye infection, fungal eye infection, viral eye infection, a nutrient deficiency, macular degeneration, glaucoma, or elevated eye pressure, including administering to an eye of a subject a composition having a plurality of lipid-polymer composite particles encapsulating a bioactive agent, wherein the lipid-polymer composite particles comprise a block copolymer, a lipid selected from the group consisting of a neutral lipid, a cationic lipid, and an anionic lipid, and a sterol, wherein the plurality of lipid-polymer composite particles has a mean particle size of between 10 and 1000 nanometers.

In another aspect, the invention features a method of treating a disease or condition selected from inflammation, pain, a bacterial infection, a fungal infection, a protozoal infection, anxiety, agitation, stress, fatigue, insomnia, mental exhaustion, memory loss, organ rejection, eczema, acne, and a skin infection, the method including administering to a subject a composition having a plurality of lipid-polymer composite particles encapsulating a bioactive agent, wherein the lipid-polymer composite particles comprise a block copolymer, a lipid selected from the group consisting of a neutral lipid, a cationic lipid, and an anionic lipid, and a sterol, wherein the plurality of lipid-polymer composite particles has a mean particle size of between 10 and 1000 nanometers.

In some embodiments of either of the above aspects, the bioactive agent is a cannabinoid or a cannabinoid derivative, a terpene, a flavonoid, an antibiotic, an antiseptic agent, an antifungal, an antibacterial, an analgesic, an anti-inflammatory agent, an antiprotozoal agent, a steroid, an antiviral agent, a lipophilic drug, an anti-VEGF agent, an anti-glaucoma agent, an essential oil, an immunogen (e.g., a vaccine component), nicotine or a nicotine analogue, cyclosporin A, tacrolimus, isotretinoin, propofol, griseofulvin or any combination thereof.

In some embodiments, the block copolymer is a poloxamer. In some embodiments, the weight ratio of the poloxamer and the bioactive agent is between 2 and 15.

In some embodiments, the lipid comprises of a carbon chain of length from 4 to 22 and a neutral, cationic, or anionic head group. In some embodiments, the lipid is a phosphatidylcholine, a phosphatidylserine, a phosphatidylglycerol, a phosphatidylethanolamine, or a phosphatidylinositol. In some embodiments, the concentration of the lipid is from about 0.1 mol % to about 10 mol %. In some embodiments, the sterol is a phytosterol, or a synthetic sterol, or cholesterol, or a cholesterol analog. In some embodiments, the concentration of the sterol is from about 5 mol % to about 50 mol % of the total lipid composition. In some embodiments, the weight ratio of the sterol to the lipid is from about 0.01 to about 0.50.

In another aspect, the invention features a method of recreational use comprising administering to a subject a composition comprising a plurality of lipid-polymer composite particles encapsulating a bioactive agent, wherein the lipid-polymer composite particles comprise a block copolymer, a lipid selected from the group consisting of a neutral lipid, a cationic lipid, and an anionic lipid, and a sterol, wherein the plurality of lipid-polymer composite particles has a mean particle size of between 10 and 1000 nanometers.

In some embodiments, of the above aspect, the bioactive agent is a recreational agent. In some embodiments, the bioactive agent is a cannabinoid or a cannabinoid derivative, a terpene, a flavonoid, an antibiotic, an antiseptic agent, an antifungal, an antibacterial, an analgesic, an anti-inflammatory agent, an antiprotozoal agent, a steroid, an antiviral agent, a lipophilic drug, an anti-VEGF agent, an anti-glaucoma agent, an essential oil, an immunogen (e.g., a vaccine component), nicotine, or a nicotine analogue, cyclosporin A, tacrolimus, isotretinoin, propofol, griseofulvin or any combination thereof. In some embodiments, the block copolymer is a poloxamer.

In some embodiments, of the any of the above aspects, the essential oil includes tea tree oil, myrrh oil, eucalyptus oil, clove oil, lavender oil, peppermint oil, Roman chamomile oil, German chamomile oil, frankincense oil, helichrysum oil, cypress oil, angelica oil, labdanum oil, petitgrain bigarade oil, orange bigarade oil, bergamot oil, sweet orange oil, palmarosa oil, lemon-scented ironbark oil, may chang oil, basil oil, sweet marjoram oil, geranium oil, patchouli oil, valerian oil, sandalwood oil, neroli bigarade oil, grapefruit oil, coriander oil, citronella oil, black peppermint oil, gully gum oil, juniper twig oil, spearmint oil, scots pine oil, rosemary oil, clary oil, ginger oil, lemon oil, mandarin oil, cumin oil, juniper berry oil, lemon balm oil, myrtle oil, Ravensara oil, sweet thyme oil, everlasting oil, manuka oil, dwarf pine oil, oregano oil, vetiver oil, Melissa oil, white fir oil, cassia oil, lemongrass oil, lime oil, wintergreen oil, fennel oil, ylang ylang oil, or a combination thereof. In some embodiments, the concentration of the essential oil is from 0.01% to 95% by weight (e.g., 5%, 10%, 15%, 20%, 25%, 30%, 35%, 40%, 45%, 50%, 55%, 60%, 65%, 70%, 75%, 80%, 85%, 90%, or 95%) of the composition. In some embodiments, the composition includes a plurality of essential oils. In some embodiments, the plurality of essential oils comprises from 2 to 10 essential oils. In some embodiments, the plurality of essential oils is from 0.01% to 95% by weight (e.g., 5%, 10%, 15%, 20%, 25%, 30%, 35%, 40%, 45%, 50%, 55%, 60%, 65%, 70%, 75%, 80%, 85%, 90%, or 95%). In some embodiments, the method includes a composition formulated as an eye drop formulation.

In some embodiments, the weight ratio of the poloxamer and the bioactive agent is between 2 and 15. In some embodiments, the lipid comprises of a carbon chain of length from 4 to 22 and a neutral, cationic, or anionic head group. In some embodiments, the lipid is a phosphatidylcholine, a phosphatidylserine, a phosphatidylglycerol, a phosphatidylethanolamine, or a phosphatidylinositol. In some embodiments, the concentration of the lipid is form about 0.1 mol % to about 10 mol %. In some embodiments, the sterol is a phytosterol, or a synthetic sterol, or cholesterol, or a cholesterol analog. In some embodiments, the concentration of the sterol is from about 5 mol % to about 50 mol % of the total lipid composition. In some embodiments, the weight ratio of the sterol to the lipid is from about 0.01 to about 0.50.

Definitions

To facilitate the understanding of this invention, a number of terms are defined below. Terms defined herein have meanings as commonly understood by a person of ordinary skill in the areas relevant to the invention. Terms such as "a," "an," and "the" are not intended to refer to only a singular entity but include the general class of which a specific example may be used for illustration. The terminology herein is used to describe specific embodiments of the invention, but their usage does not limit the invention, except as outlined in the claims.

As used herein, any values provided in a range of values include both the upper and lower bounds, and any values contained within the upper and lower bounds.

As used herein, term "about," as used herein, refers to ±10% of a recited value. The term "administer" means to introduce a formulation of the present invention into the body of a patient in need thereof to treat a disease or condition.

The term "bioactive agent" as used herein refers to any synthetic or naturally occurring compound (in free form, salt form or solvated or hydrated form) having a desired biological or physiological effect, such as a protein, drug, antigen, nutrient, cosmetic, fragrance, flavoring, diagnostic, pharmaceutical, vitamin, or dietary agent and will be formulated at a level sufficient to provide an in vivo concentration at a functional level (including local concentrations for topical compositions). Under some circumstances one or more of components of the lipid matrix i) (e.g., components (a), (b), (c) and/or (d)) may also be an active agent, although it is preferred that the optional bioactive agent (iii) should not be one of these components (e.g., should not be a component of the lipid matrix). Most preferred active agents are pharmaceutical agents (e.g., APIs) including drugs, vaccines, and diagnostic agents.

The term "block copolymer" as used herein, refers to a linear polymer having regions or blocks along its backbone chain which are characterized by similar hydrophilicity, hydrophobicity, or chemistry.

The term "diblock copolymer" means a block copolymer comprising two blocks.

The term "triblock copolymer" means a block copolymer comprising three blocks.

The term "multiblock copolymer" means a block copolymer comprising a plurality of blocks.

As used herein, the term "encapsulate," "encapsulated," or "encapsulating" refers to an enclosure of a moiety (e.g., a bioactive agent as defined herein) within an enclosed polymer assembly structure, e.g., a micelle. An encapsulated bioactive agent (e.g., an encapsulated cannabinoid) is enclosed by the polymer assembly structure, e.g., such an encapsulated moiety is located in the hydrophobic interior of the polymer assembly structure (e.g., the lumen of a micelle).

The term "anionic head group," as used herein, refers to a lipid head group that carries a net negative charge at physiological pH.

The term "cationic head group," as used herein, refers to a lipid head group that carries a net positive charge at physiological pH.

The term "neutral head group," as used herein, refers to a lipid head group that exists in an uncharged form at physiological pH.

As used herein, "lipid nanoparticle" or "LNP" is a vesicle that includes a lipid layer encapsulating a substantially solid lipid core; the lipid core can contain a pharmaceutically active molecule. LNPs typically contain a cationic lipid, a non-cationic lipid, and a lipid that prevents aggregation of the particle (e.g., a PEG-lipid conjugate).

As used herein, the term "lipid-polymer composite particle" refers to a complex of molecules held together by noncovalent bonds, such as hydrogen bonds, Van der Waals forces, electrostatic interactions, hydrophobic effect, and Pi-Pi interactions. Lipid-polymer composite particles may include large complexes of molecules that form, e.g., sphere-like structures. Lipid-polymer composite particles include, for example, lipid nanoparticles and micelles.

As used herein, the term "micelle," "micellar" or variants thereof, refers to a polymer assembly comprised of a hydrophilic shell (or corona) and a hydrophobic and/or ionic interior. In addition, the term micelle may refer to any poly ion complex assembly consisting of a multiblock copolymer possessing a net positive charge and a suitable negatively charged polynucleotide.

The term "nanoparticle," as used herein, refers to a polymer-based particle having a diameter in the nanometer range (e.g., 1nm-1000nm).

The term "nutraceutical agent" refers to any substance that is a food or a part thereof, and/or conferring extra health benefits in addition to the basic nutritional value found in foods. For example, nutraceutical agents may contain components from food sources. Exemplary nutraceutical agents include, but are not limited to, antioxidants, dietary supplements, fortified dairy products, plant extracts, vitamins, minerals, and herbals.

The term "plurality," as used herein, means more than one, such as at least 2, 20, 50, 100, 1000, 10000, 100000, 1000000, 10000000 or even more.

As used herein, the terms "recreational agent" or "recreational substance" or variations thereof, refer to compounds useful in providing relaxing, enjoyable, and entertaining activity for a subject.

The term "subject," as used herein, can be a human, non-human primate, or other mammal, such as but not limited to dog, cat, horse, cow, pig, turkey, goat, fish, monkey, chicken, rat, mouse, and sheep.

As used herein, the term "sterol" includes all sterols without limitation, for example: sitosterol, campesterol, stigmasterol, brassicasterol (including dihydrobrassicasterol), desmosterol, chalinosterol, poriferasterol, clionasterol, ergosterol, coprosterol, codisterol, isofucosterol, fucosterol, clerosterol, nervisterol, lathosterol, stellasterol, spinasterol, chondrillasterol, peposterol, avenasterol, isoavenasterol, fecosterol, pollinastasterol, cholesterol and all natural or synthesized forms and derivatives thereof, including isomers. It is to be understood that modifications to the sterols i.e. to include side chains also falls within the purview of this invention.

The term "therapeutic agent" refers to any substance having therapeutic properties that produce a desired, usually beneficial, effect. For example, therapeutic agents may treat, ameliorate, and/or prevent disease. Such agents can be synthetic or naturally occurring, non-peptide, proteins or peptides, oligonucleotides or nucleotides, polysaccharides or sugars.

"Vesicles" are defined herein as a type of a lipid-polymer composite particle in which amphipathic molecules (e.g., lipids) collectively define a volume, e.g., a substantially spherical volume. Amphipathic molecules (e.g., lipids) typically make up at least one shell of a vesicle. In this shell, the amphipathic molecules are arranged in a bilayer with hydrophilic portions of the amphipathic molecules being outwardly directed relative to the plane of the bilayer and the hydrophobic portions of the amphipathic molecules being disposed predominantly within the bilayer. The converse arrangement exists if the surrounding medium is hydrophobic.

BRIEF DESCRIPTION OF THE DRAWINGS

FIG. 3 is a table showing the effective diameter and polydispersity of formulations Fc1-Fc7. Formulations Fc1, Fc2, and Fc9 where loaded with 0.02% w/w CBD. Formulations Fc3-Fc8 were loaded with 0.25% w/w CBD. Mean and standard deviation values are reported.

FIG. 4 is a table showing the mean and standard deviation values of measured zeta potential of particles in formulations Fc1-Fc9.

Formulations Fe1, Fe4, and Fe7 were prepared by poloxamer homogenization followed by 0.5% CBD w/w and phospholipid and cholesterol added via ethanol injection. Formulations Fe2, Fe5, and Fe8 were prepared by poloxamer homogenization with 0.5% CBD w/w followed by phospholipid and cholesterol addition via ethanol injection. Formulations Fe3, Fe6, and Fe9 were prepared by poloxamer homogenization with 0.5% CBD w/w followed by phospholipid and cholesterol addition in powder form.

Figure 12:
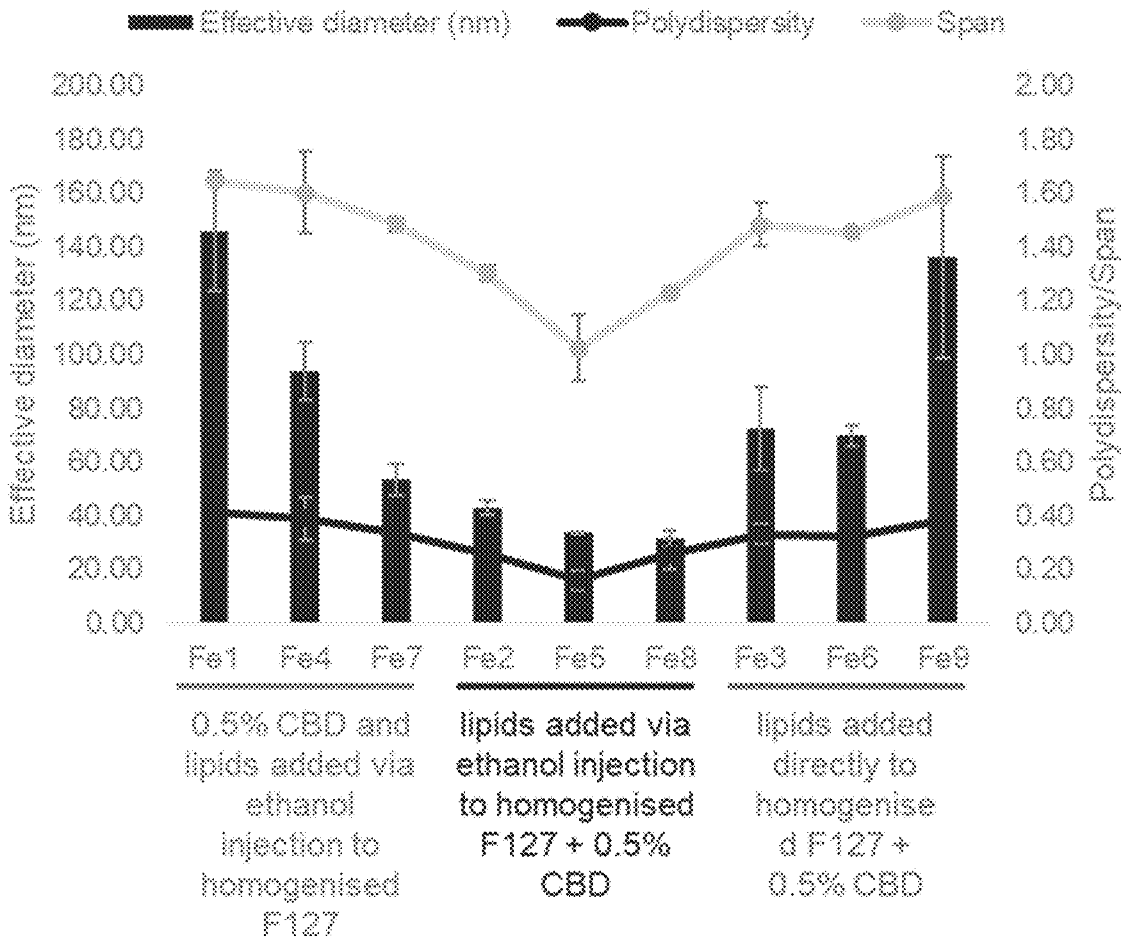

FIG. 12 is graph showing the particle size, polydispersity and span values of lipid-polymer composite particles in formulations Fe1-Fe9.

Figure 13:
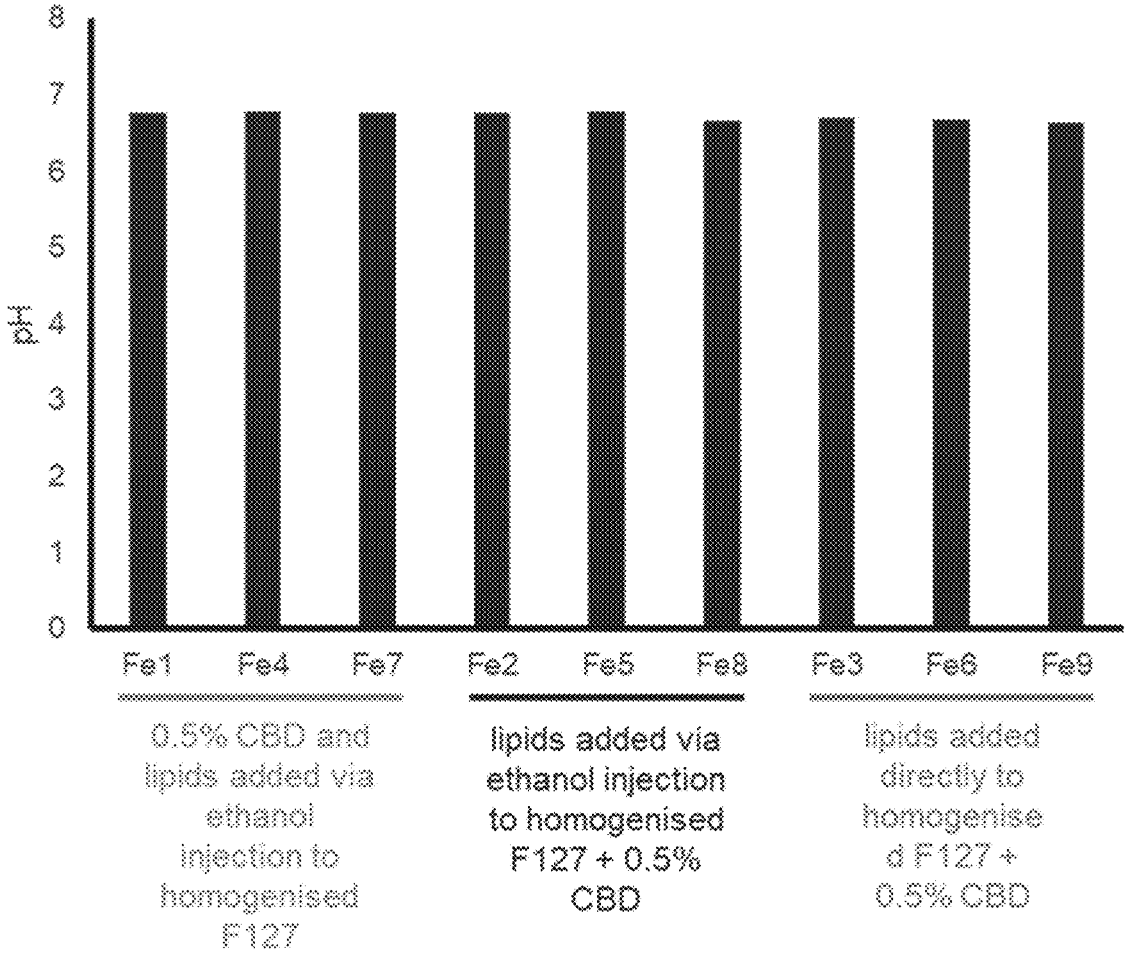

FIG. 13 is graph showing the pH of formulations Fe1-Fe9. All formulations had pH near neutral.

FIG. 14 is table showing the tonicity of formulations Fe1-Fe9 compared to the tonicity of saline, control poloxamer and CBD suspensions and three commercially available eye drop solutions HYABAK® 0.15%, THEALOZ® DUO New, and THEALOZ® DUO.

Figure 15:
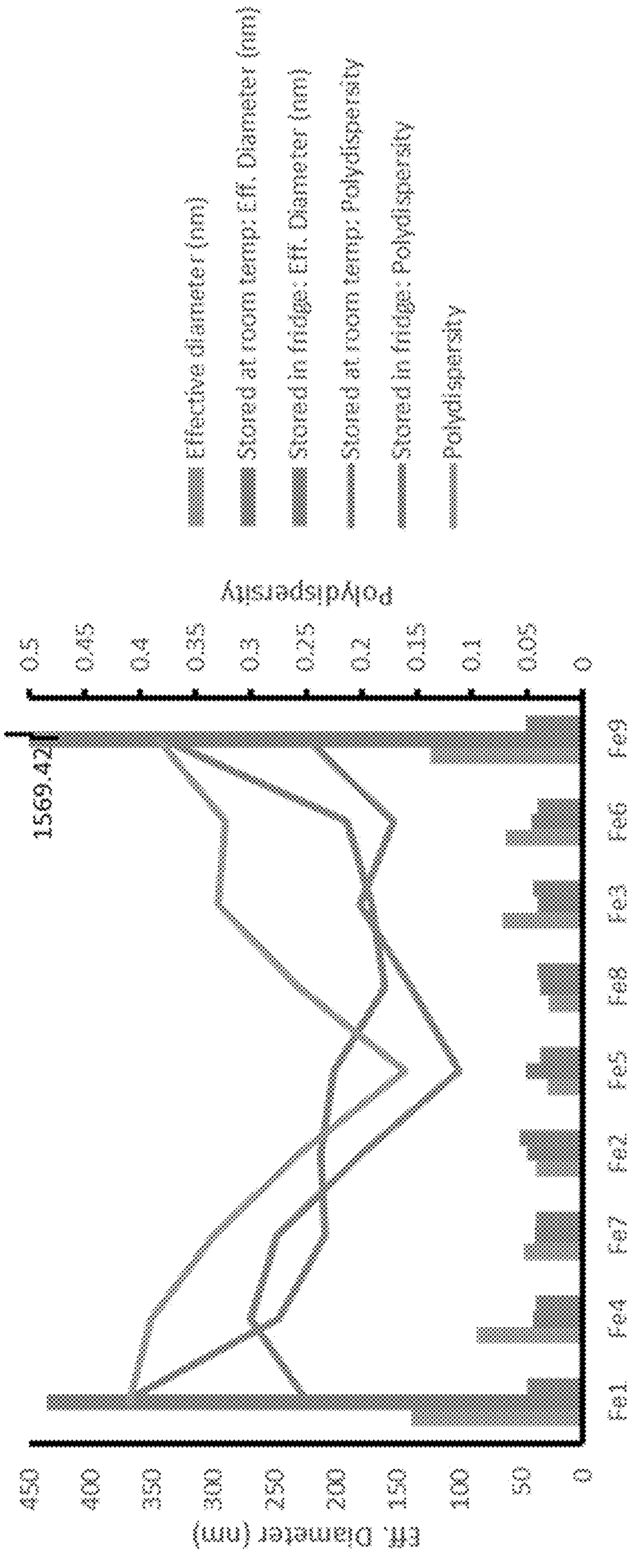

FIG. 15 is graph showing is graph showing the size stability of formulations Fe1-Fe9. The effective diameter and polydispersity were calculated for all formulations on the day of preparation (bar on the left), and 19 days after preparation when stored in either room temperature 20° C. (bar in the middle) or at 4° C. (bar on the right).

Figure 16:
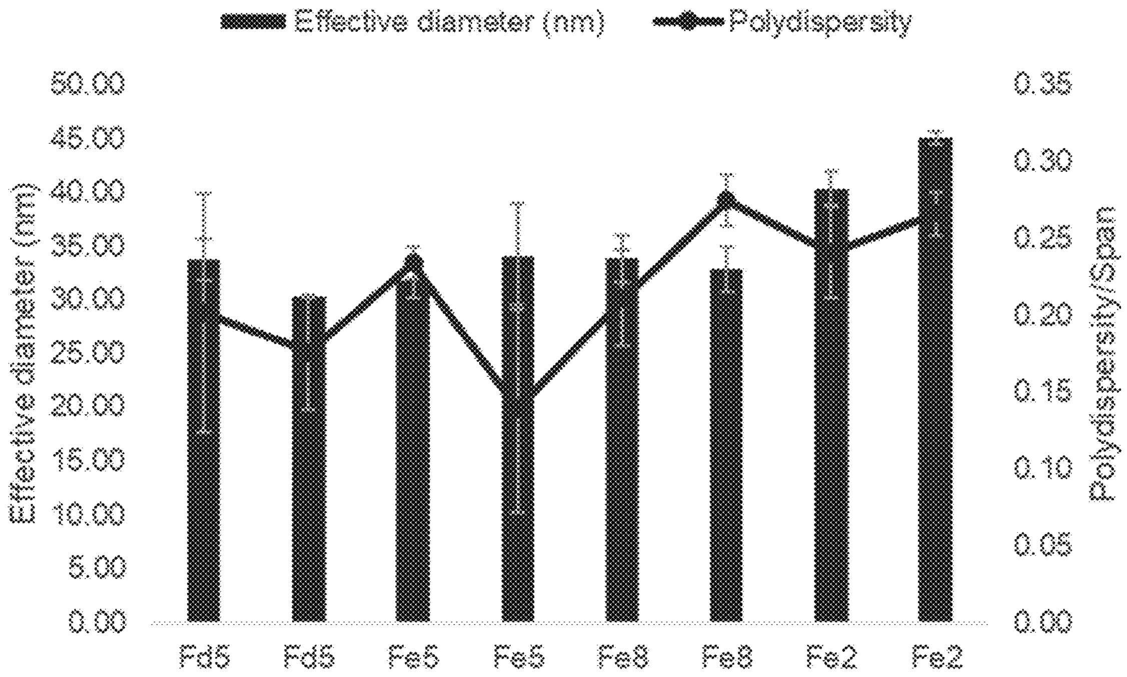

FIG. 16 is graph showing particle size, polydispersity, and span values of optimized formulations Fd5, Fe5, Fe8, and Fe2.

Figure 17:
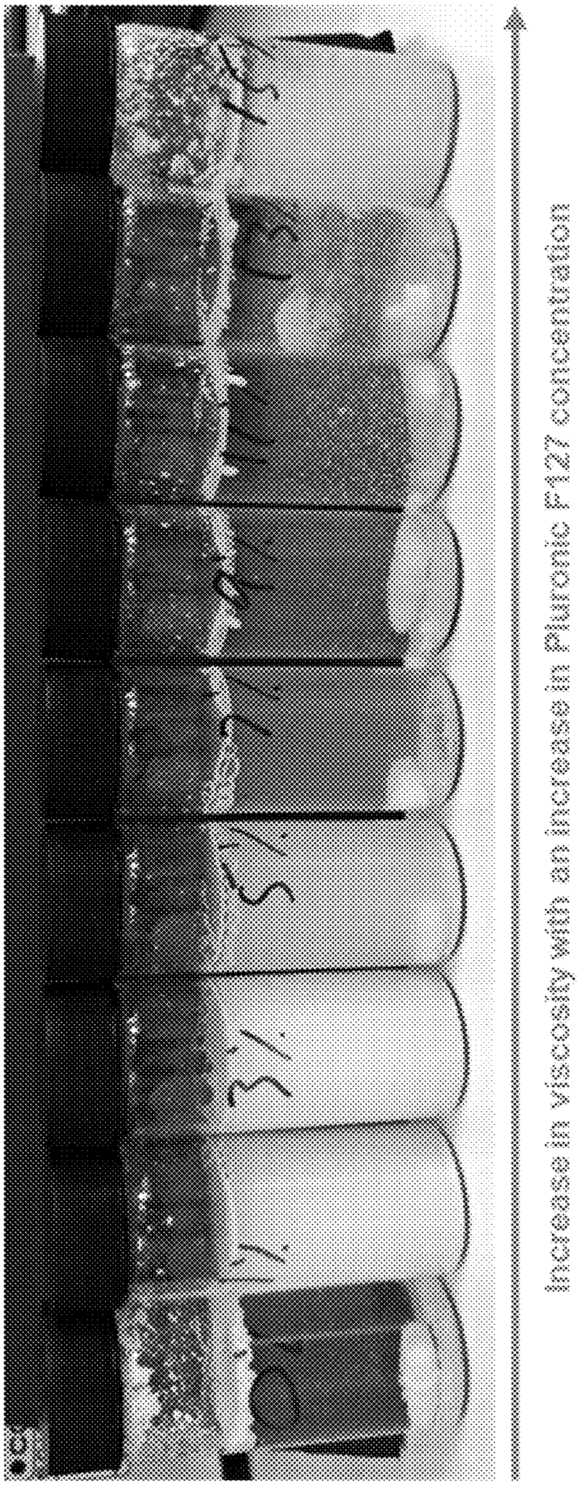

FIG. 17 is a photographic image showing excess CBD stirred into formulations containing PLURONIC® F127 in concentrations of 1, 3, 5, 7, 9, 11, 13 and 15% w/v. The vial in the far left contained no PLURONIC® F127 and served as a control. The viscosity of the formulations increased with an increase in concentration of PLURONIC® F127.

Figure 18:
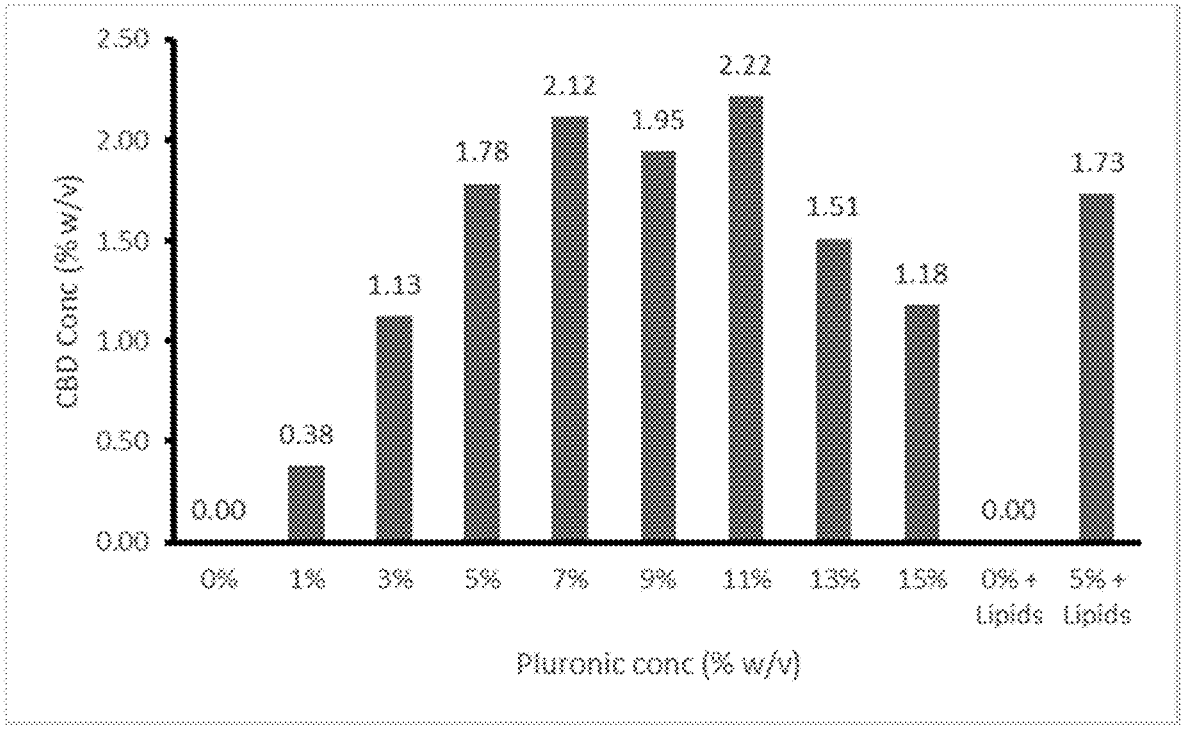

FIG. 18 is a graph showing the saturated solubility of CBD in water (0%), 1, 3, 5, 7, 9, 11, 13, 15% PLURONIC® F127, lipids only (0%+Lipids) and 5% PLURONIC® F127 with lipids (5%+Lipids). Lipid concentration used was 0.21 mM DSPC and 0.19 mM cholesterol. The solubility of CBD increased with increasing concentration PLURONIC® F127, peaking around 7-11% PLURONIC® F127. There was no substantial difference in the solubility of CBD with the incorporation of lipids at the lipid concentrations used.

Figure 19:
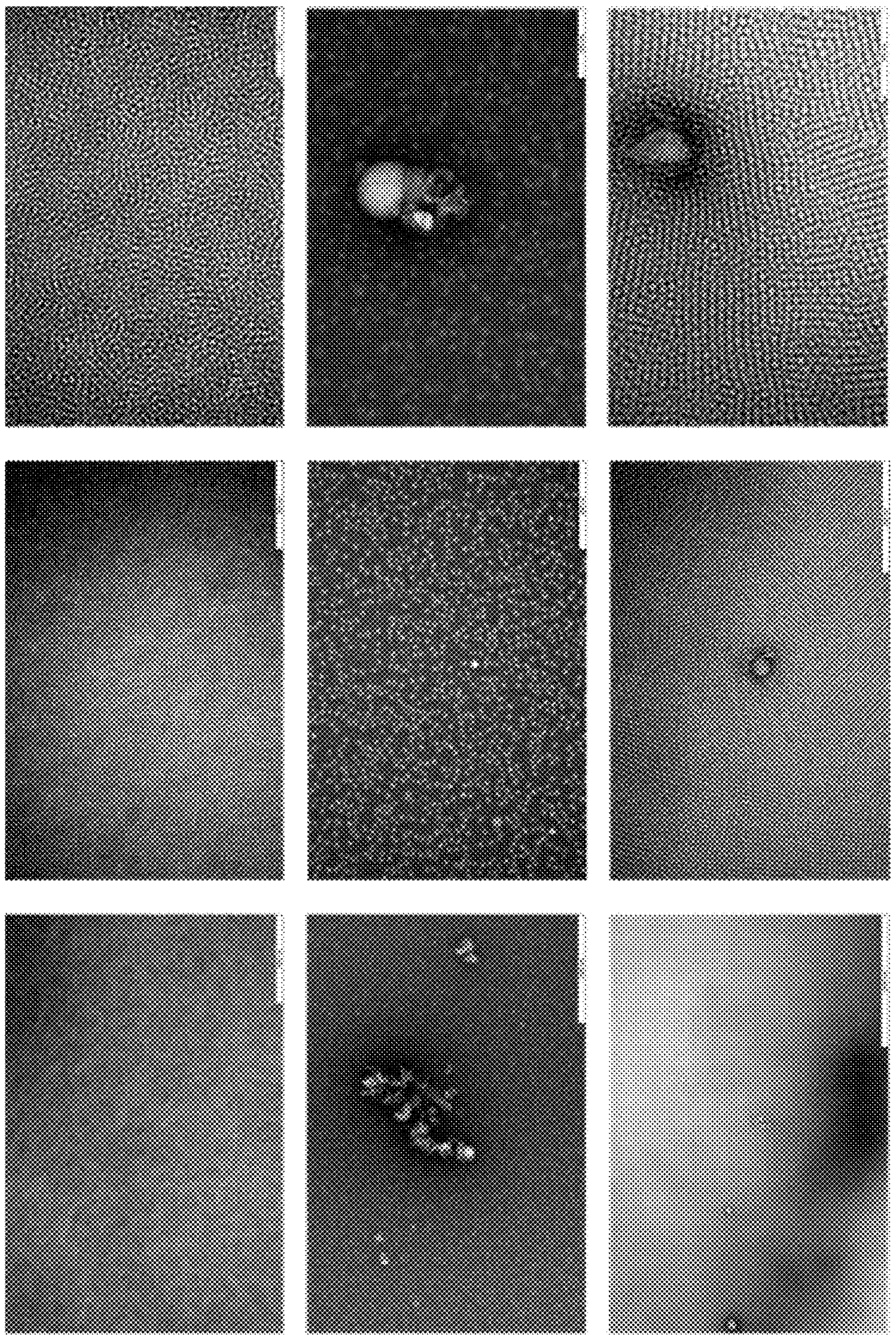

FIG. 19 is a series of transmission electron microscopy (TEM) images of three different formulations containing CBD. In 5% PLURONIC® F127 formulations (top row), closely packed spherical structures ranging from 20-30 μm in diameter were observed. These were most likely micelles. In lipid only formulations (middle row) (DSPC:Chol; (0.21: 0.19Mm)) two distinct features were observed, smaller diffuse spherical structures and larger clumped structures. In formulations containing both lipids and PLURONIC® F127 (bottom row) (5% PLURONIC®F127+DSPC:Chol (0.21: 0.19 mM)) also two distinct features were observed. Closely packed micellar structures of 20-30 μm and larger unilamellar and multilamellar structures with smaller micelles encapsulated within them were observed.

Figure 20:
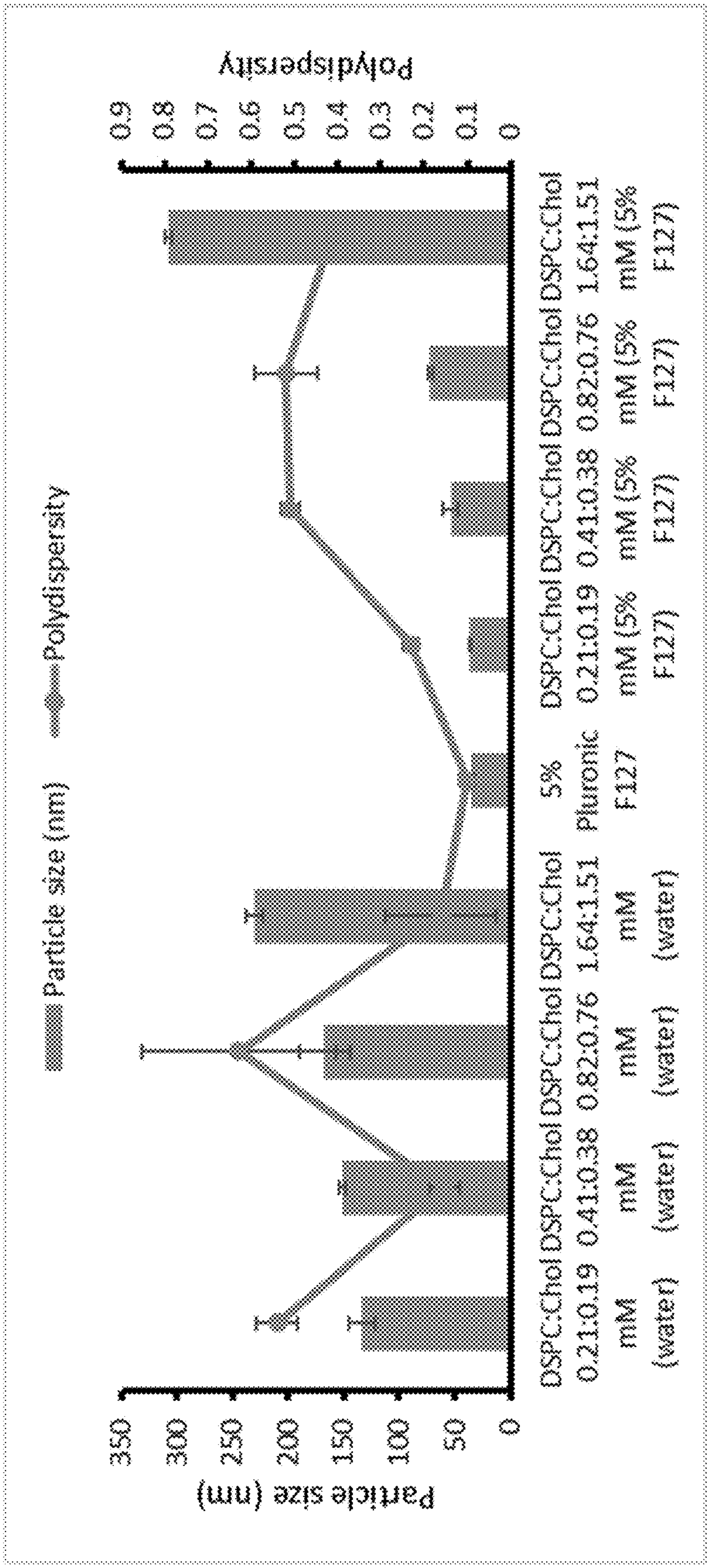

FIG. 20 is a graph showing particle size and polydispersity of formulations containing higher concentrations of DSPC and cholesterol. Generally particle size was observed to be higher in the absence of PLURONIC® F127 compared to when PLURONIC® F127 is combined with DSPC:Chol in concentrations of 1.64:1.51 mM. Also, of note was that particle size increased with increasing concentration of lipids in PLURONIC® F127 containing formulations.

Figure 21:
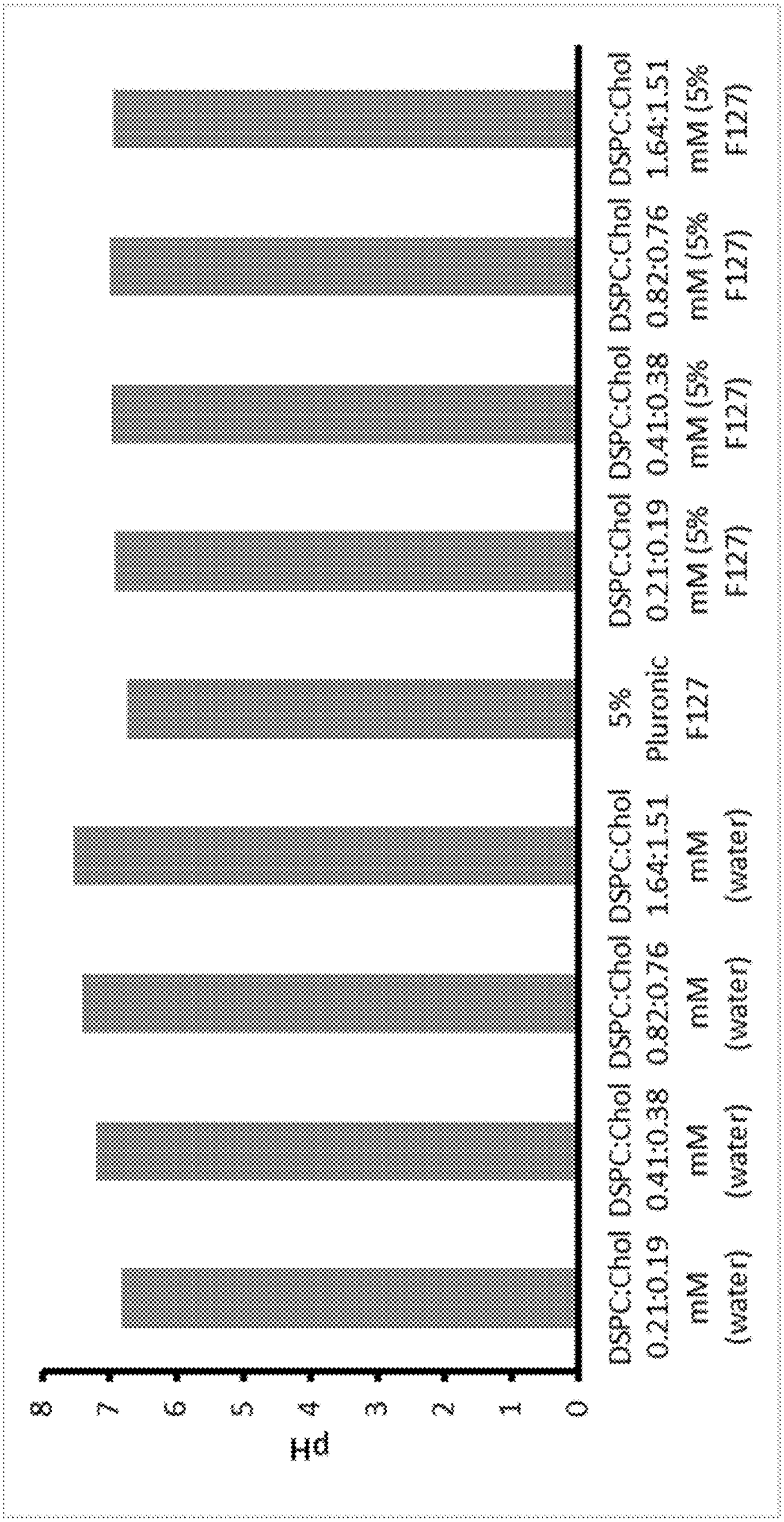

FIG. 21 is a graph showing no substantial differences in pH of formulations with or without PLURONIC® F127 and the pH also did not change substantially with increasing concentrations of lipids (DSPC and cholesterol).

Figure 22:
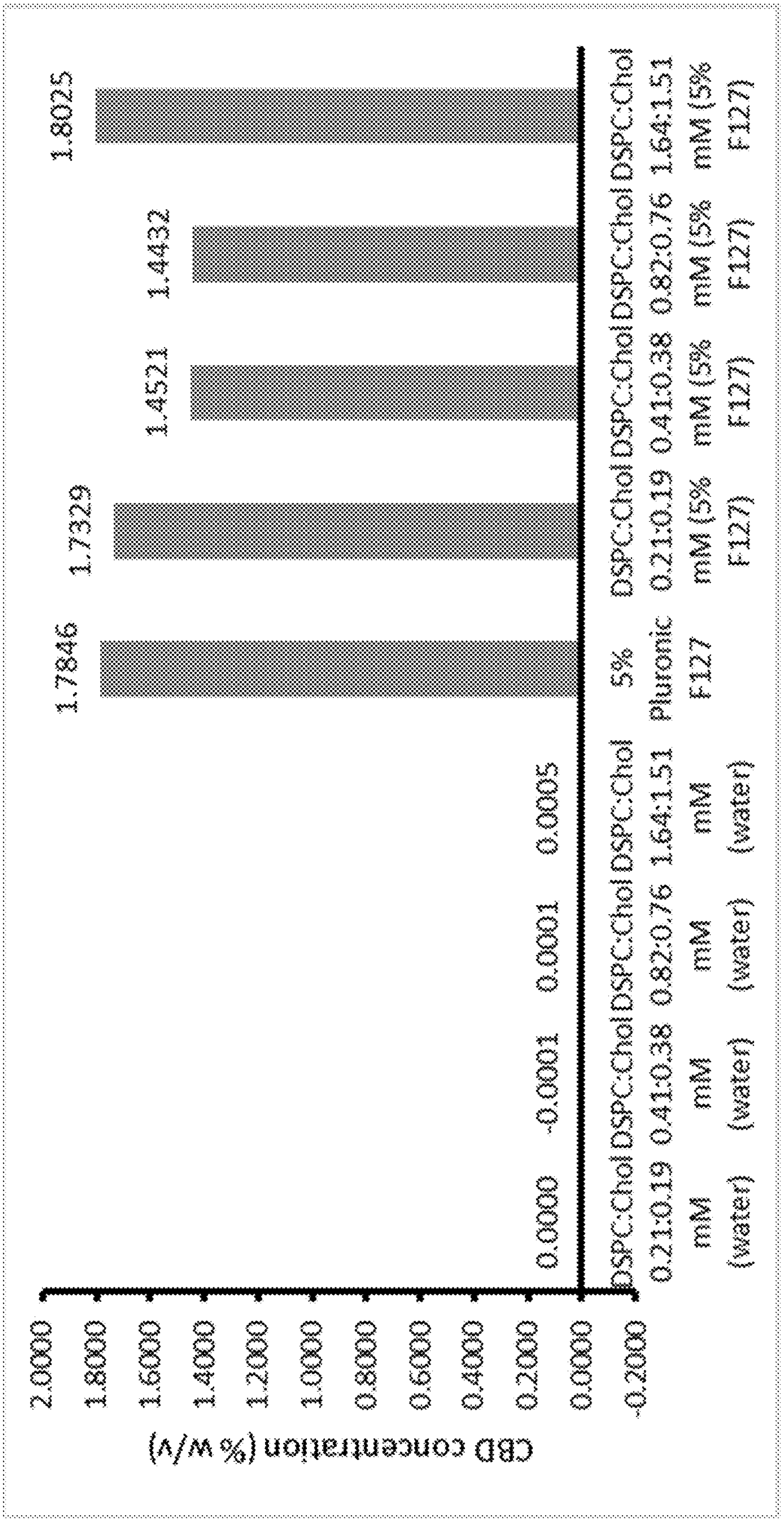

FIG. 22 is a graph showing CBD dissolved in formulations lacking (left) and containing PLURONIC® F127 (right) with increasing concentrations of lipids.

Figure 23:
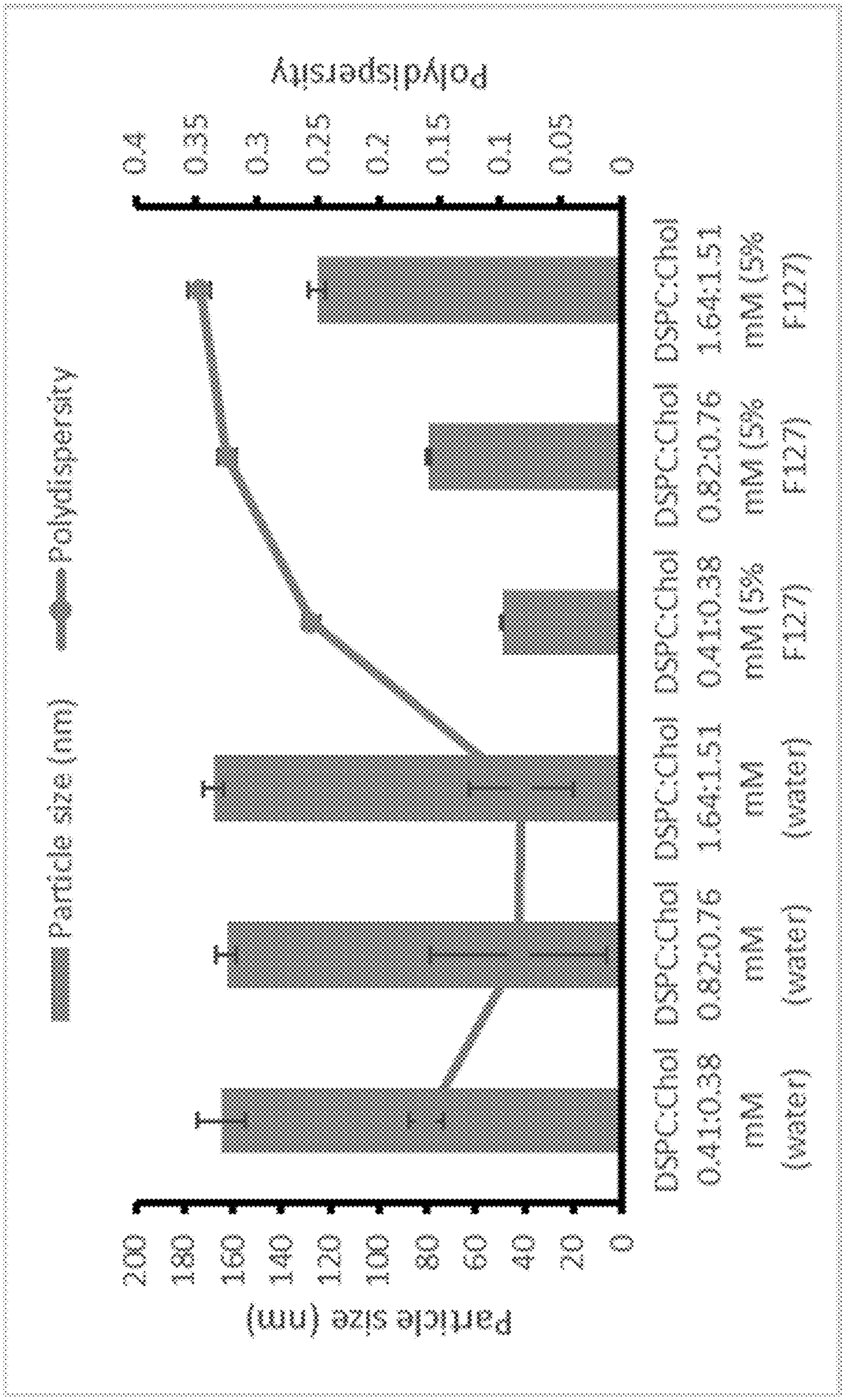

FIG. 23 is a graph showing particle size and polydispersity of formulations containing higher concentrations of lipids (DSPC and cholesterol). Again, particle size was higher without PLURONIC® F127 and it increased as the concentration of lipids in PLURONIC® F127 formulations increased.

Figure 24:
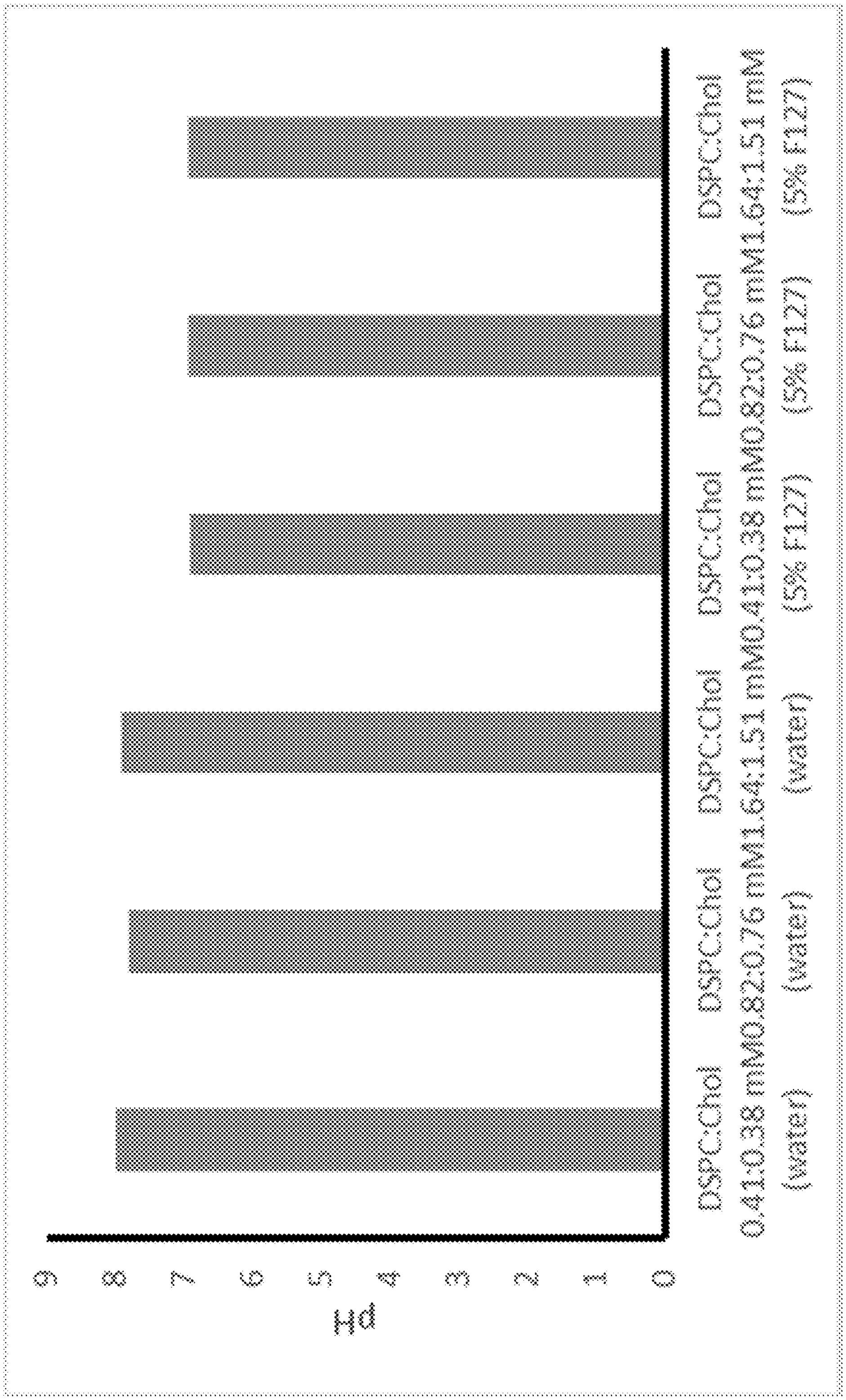

FIG. 24 is a graph showing no substantial differences in pH of formulations with or without PLURONIC® F127 and the pH also did not change substantially with increasing concentrations of lipids.

Figure 25:
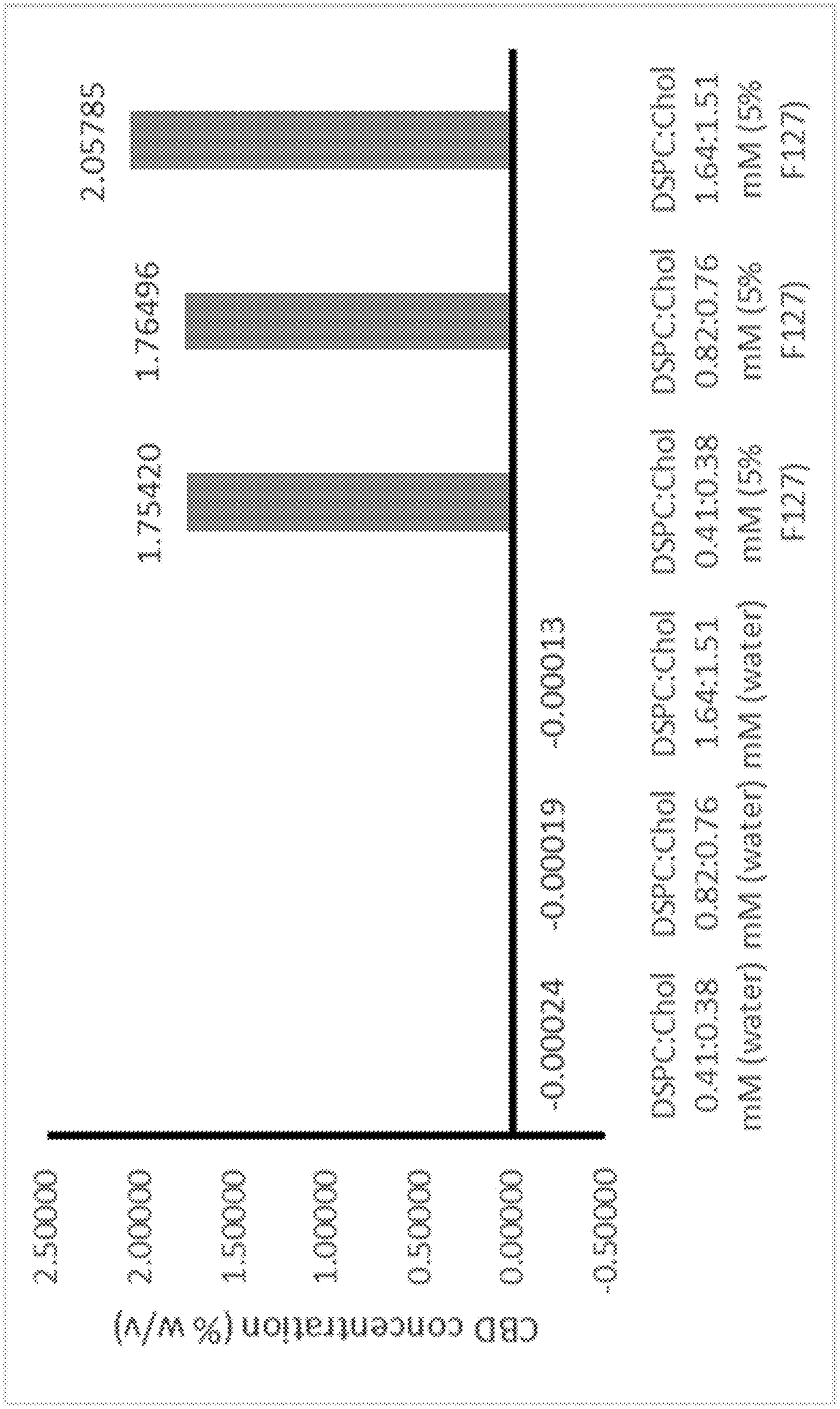

FIG. 25 is a graph showing CBD dissolved in formulations lacking (left) and containing (right) PLURONIC® F127 with increasing concentrations of lipids (DSPC and cholesterol).

DETAILED DESCRIPTION

The present invention features new lipid-polymer composite particles that are useful for the formulation of bioactive agents for administration to a subject, e.g., a human subject. The lipid-polymer composite particles include a plurality of (e.g., at least 2, 3, 4, 5, 6, 7, 8, 9, 10, 20, 30, 40, 50, 100, 1,000, 10,000, 100,000, 1,000,000, 10,000,000, or more) nanoparticles that encapsulate a bioactive agent. The nanoparticles include a block copolymer, a lipid, e.g., phospholipid, and a sterol. The formulations of a bioactive agent (e.g., a therapeutic agent, a nutraceutical agent, or a recreational agent) described herein provide for easier loading of lipid-polymer composite particles with higher drug loading capacity, increased stability of the formulations, and lower surface tension of water, which allows for lipid coating and entrapment. This improved process for preparing lipid-polymer composite particles, e.g., micelles, with a lipid coating allows aqueous loading of hydrophobic bioactive agents as well as controlled drug release. Furthermore, the compositions and methods described herein avoid the use of organic solvents e.g., ethanol, to solubilize hydrophobic bioactive agents. The components of the formulations are described in more detail below.

Lipid-Polymer Composite Particles

Lipid-polymer composite particles may be used to formulate a bioactive agent (e.g., a therapeutic agent, a nutraceutical agent, or a recreational agent, e.g., a cannabinoid) for delivery. Lipid-polymer composite particles include a defined complex of molecules (e.g., lipids and polymers) held together by noncovalent bonds, such as hydrogen bonds, Van der Waals forces, electrostatic interactions, hydrophobic effect, and Pi-Pi interactions. Lipid-polymer composite particles may include large complexes of molecules that form sphere-, rod-, or sheet-like structures. Lipid-polymer composite particles include, for example, micelles and LNPs. Lipid-polymer composite particles may have a predetermined size. The size of the structure may vary based on the components (e.g., size or number of molecules of the bioactive agent) packed within the structure.

The size of the lipid-polymer composite particle may vary from, e.g., about 10 nm to about 1,000 nm. Non-limiting examples of the Z-average mean particle diameters include, e.g., from about 10 nm to about 500 nm, from about 10 nm to about 100 nm, from about 500 nm to about 1000 nm. For example, the lipid-polymer composite particle may have a Z-average mean particle diameter of, e.g., about 10 nm, about 15 nm, bout 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, about 205 nm, about 210 nm, about 215 nm, about 220 nm, about 225 nm, about 230 nm, about 235 nm, about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, about 305 nm, about 310 nm, about 315 nm, about 320 nm, about 325 nm, about 330 nm, about 335 nm, about 340 nm, about 345 nm, about 350 nm, about 355 nm, about 360 nm, about 365 nm, about 370 nm, about 375 nm, about 380 nm, about 385 nm, about 390 nm, about 395 nm, about 400 nm, about 405 nm, about 410 nm, about 415 nm, about 420 nm, about 425 nm, about 430 nm, about 435 nm, about 440 nm, about 445 nm, about 450 nm, about 455 nm, about 460 nm, about 465 nm, about 470 nm, about 475 nm, about 480 nm, about 485 nm, about 490 nm, about 495 nm, about 500 nm, about 505 nm, about 510 nm, about 515 nm, about 520 nm, about 525 nm, about 530 nm, about 535 nm, about 540 nm, about 545 nm, about 550 nm, about 555 nm, about 560 nm, about 565 nm, about 570 nm, about 575 nm, about 580 nm, about 585 nm, about 590 nm, about 595 nm, about 600 nm, about 605 nm, about 610 nm, about 615 nm, about 620 nm, about 625 nm, about 630 nm, about 635 nm, about 640 nm, about 645 nm, about 650 nm, about 655 nm, about 660 nm, about 665 nm, about 670 nm, about 675 nm, about 680 nm, about 685 nm, about 690 nm, about 695 nm, about 700 nm, about 705 nm, about 710 nm, about 715 nm, about 720 nm, about 725 nm, about 730 nm, about 735 nm, about 740 nm, about 745 nm, about 750 nm, about 755 nm, about 760 nm, about 765 nm, about 770 nm, about 775 nm, about 780 nm, about 785 nm, about 790 nm, about 795 nm, about 800 nm, about 805 nm, about 810 nm, about 815 nm, about 820 nm, about 825 nm, about 830 nm, about 835 nm, about 840 nm, about 845 nm, about 850 nm, about 855 nm, about 860 nm, about 865 nm, about 870 nm, about 875 nm, about 880 nm, about 885 nm, about 890 nm, about 895 nm, about 900 nm, about 905 nm, about 910 nm, about 915 nm, about 920 nm, about 925 nm, about 930 nm, about 935 nm, about 940 nm, about 945 nm, about 950 nm, about 955 nm, about 960 nm, about 965 nm, about 970 nm, about 975 nm, about 980 nm, about 985 nm, about 990 nm, about 995 nm, or about 1000 nm.

The mean particle diameter may be measured by zeta potential, dynamic light scattering (DLS), electrophoretic light scattering (ELS), static light scattering (SLS), molecular weight, electrophoretic mobility, size exclusion chromatography (SEC), field flow fractionation, or other methods known in the art. In particular embodiments, the lipid-polymer composite particle contains a Z-average mean particle diameter of from about 10 nm to about 100 nm. One of skill in the art would appreciate that a population of lipid-polymer composite particles (e.g., LNPs, or micelles) may have a range of Z-average mean particle diameters within the population. Thus, the population may be polydisperse. The population may have a polydispersity index of 0.3 or less (e.g., 0.05 to 0.3). The polydispersity index can be determined using DLS (see, e.g., ISO 22412:2017).

Lipid Nano Particles

Bioactive agents of the invention may be fully encapsulated in a lipid formulation, e.g., an LNP, or another lipid-polymer composite particle. LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 2000/003683. LNPs may have a mean diameter of about 50 nm to about 150 nm, more typically about 60 nm to about 130 nm, more typically about 70 nm to about 110 nm, most typically about 70 nm to about 90 nm, and are substantially nontoxic. In addition, the bioactive agents when present in the LNPs of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to bioactive agent ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

Non-limiting examples of cationic lipids include N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyI)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.CI), 1,2-Dilinoleoyl-3-trimethylaminopropane chloride salt (DLin-TAP.CI), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyetetrahydro-3aH-cyclopenta[d][1,3]dioxol-5-amine (ALN100), (6Z,9Z,28Z,31Z)-heptatriaconta-6,9,28,31-tetraen-19-yl4-(dimethylamino)butanoate (MC3), 1,1'-(2-(4-(2-((2-(bis(2-hydroxydodecyl)amino)ethyl)(2-hydroxydodecyl)amino) ethyl)piperazin-1-yeethylazanediyedidodecan-2-ol (Tech G1), or a mixture thereof. The cationic lipid can comprise, for example, from about 20 mol % to about 50 mol % or about 40 mol % of the total lipid present in the particle.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoylphosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be, for example, from about 5 mol % to about 90 mol %, about 10 mol %, or about 60 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be, for example, from 0 mol % to about 20 mol % or about 2 mol % of the total lipid present in the particle.

The lipid can have a carbon chain of length of from 4 to 22 and a neutral, cationic, or anionic head group.

In some embodiments, the particle further includes a sterol, (e.g., cholesterol) at, e.g., about 10 mol % to about 60 mol % or about 50 mol % of the total lipid present in the particle.

Micelles

Micelles are a particular type of molecular assembly in which amphipathic molecules are arranged in a spherical structure such that all the hydrophobic portions of the molecules are directed inward, leaving the hydrophilic portions in contact with the surrounding aqueous phase. Micelles may be made of lipids. The micelle phase is caused by the packing behavior of single-tail lipids in a bilayer. The difficulty filling all the volume of the interior of a bilayer, while accommodating the area per head group forced on the molecule by the hydration of the lipid head group, leads to the formation of the micelle. This type of micelle is known as a normal-phase micelle (oil-in-water micelle). Inverse micelles have the head groups at the center with the tails extending out (water-in-oil micelle).

Micelles are approximately spherical in shape. Other phases, including shapes such as ellipsoids, cylinders, and bilayers, are also possible. The shape and size of a micelle are a function of the molecular geometry of its surfactant molecules and solution conditions such as surfactant concentration, temperature, pH, and ionic strength. The process of forming micelles is known as micellization and forms part of the phase behavior of many lipids according to their polymorphism.

Phospholipids

The lipid-polymer composite particles described herein may include one or more phospholipids. Phospholipids generally consist of two hydrophobic fatty acid tails and a hydrophilic head with a phosphate group. The two components are usually joined together by a glycerol molecule. The phosphate groups can be modified with organic molecules such as choline, ethanolamine or serine. Suitable phospholipids that may be used in the compositions described herein include, for example, phosphatidylcholine, phosphatidylserine, phosphatidylglycerol, phosphatidylethanolamine, phosphatidylinositol. The concentration of the phospholipid in the lipid-polymer compositive particles may be from about 2% to about 20% v/v (e.g., from about 4% to about 18%, from about 5% to about 15%, e.g., about 10%).

Block Copolymers

The lipid-polymer composite particles described herein may include block copolymers. Block copolymers refer to a linear polymer having regions or blocks along its backbone chain that are characterized by similar hydrophilicity, hydrophobicity, or chemistry. Block copolymers may include, e.g., two, three, four, or more blocks (e.g., diblock or triblock copolymers). Multiblock copolymers include a plurality of blocks.

Diblock Copolymers

The compositions described herein may include a diblock copolymer, which includes two distinct blocks of repeating polymer units. One example of a diblock copolymer as described herein includes an amphipathic copolymer, such as one with a region including a hydrophilic chain of repeated units connected to a region including a hydrophobic chain of repeating units with or without a linker. Such a diblock copolymer may include a hydrophilic chain of polyoxyethylene (PEO) subunits connected to a hydrophobic chain of polyoxypropylene (PPO) subunits. The diblock copolymer of PEO and PPO subunits can be represented by the following formula: $X_1(C_2H_4O)_m$-L-$(C_3H_6O)_nX_2$. $X_1$ and $X_2$ may be any chemical moiety. L may be a linker that may optionally be present. In some embodiments, the PEO and PPO subunit blocks are directly covalently linked. In some embodiments, $X_1$ and $X_2$ are H and OH, respectively. Other diblock copolymers include, for example, poly(ethylene glycol)-poly(γ-benzyl L-glutamate) PEG-PBLA, poly(ethylene glycol)-poly(D,L-lactic acid) PEG-PDLLA, poly(ethylene glycol)-poly(L-lactic acid) PEG-PLLA, poly(ethylene glycol)-poly(c-caprolactone) PEG-PCL, poly(ethylene glycol)-poly(D,L-lactide-co-glycolide) PEG-PLGA, poly(ethylene glycol)-poly (γ-benzyl L-glutamate) PEG-PBLG, poly (ethylene glycol)-poly(β-benzyl L-aspartate) PEG-PBLA, poly(ethylene glycol)-poly(α-benzyl carboxylate-ε-caprolactone) PEG-PBCL, and poly(ethylene glycol)-poly(δ-valerolactone) PEG-PVL. For clarity, as used herein, $X_1$-[PEO]-L-[PPO]-$X_2$ refers to a structure:

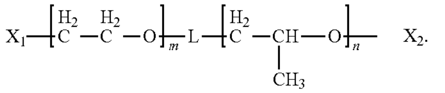

The lengths of the polymer blocks can be customized. As a result, many different diblock copolymers exist. Diblock copolymers suitable for use in conjunction with the compositions and methods of the present disclosure include those having an average molecular weight of from about 5 kDa to about 30 kDa (e.g., 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, or 30 kDa. Since the synthesis of diblock copolymers is associated with a natural degree of variation from one batch to another, the numerical values recited above (and those used herein to characterize a given diblock copolymer) may not be precisely achievable upon synthesis, and the average value will differ to a certain extent. Thus, the term "diblock copolymer" as used herein can be used interchangeably with the term "diblock copolymers" (representing an entity of several diblock copolymers, also referred to as mixture of diblock copolymers) if not explicitly stated otherwise. The term "average" in relation to the number of monomer units or molecular weight of (a) diblock copolymer(s) as used herein is a consequence of the technical inability to produce diblock copolymers all having the identical composition and thus the identical molecular weight. Diblock copolymers produced according to state-of-the-art methods will be present as a mixture of diblock copolymers each showing a variability as regards their molecular weight, but the mixture as a whole averaging the molecular weight specified herein.

Poloxamers

One example of a triblock copolymer is a poloxamer. A poloxamer refers to a non-ionic triblock copolymer composed of a central hydrophobic chain of polyoxypropylene flanked by two hydrophilic chains of polyoxyethylene. Poloxamers are also known by the trade name of "PLURONIC®" or "SYNPERONIC®" (BASF). The block copolymer can be represented by the following formula: $HO(C_2H_4O)_x(C_3H_6O)_y(C_2H_4O)_zH$. The lengths of the polymer blocks can be customized. As a result, many different poloxamers exist. Since the synthesis of block copolymers is associated with a natural degree of variation from one batch to another, the numerical values used herein to characterize a given poloxamer may not be precisely achievable upon synthesis, and the average value will differ to a certain extent. Thus, the term "poloxamer" as used herein can be used interchangeably with the term "poloxamers" (representing an entity of several poloxamers, also referred to as mixture of poloxamers) if not explicitly stated otherwise. The term "average" in relation to the number of monomer units or molecular weight of (a) poloxamer(s) as used herein is a consequence of the technical inability to produce poloxamers all having the identical composition and thus the identical molecular weight. Poloxamers produced according to state-of-the-art methods will be present as a mixture of poloxamers each showing a variability as regards their molecular weight, but the mixture as a whole averaging the molecular weight specified herein. Poloxamers suitable for use with the compositions described herein are disclosed in Alexandridis and Bodratti, Journal of Functional Materials 9 (1):11 (2018), the disclosure of which is incorporated herein by reference in its entirety.

Poloxamers that may be used in conjunction with the compositions and methods of the disclosure include those having an average molar mass of polyoxypropylene subunits of greater than 2,050 g/mol (e.g., an average molar mass of polyoxypropylene subunits of about 2,055 g/mol, 2,060 g/mol, 2,075 g/mol, 2,080 g/mol, 2,085 g/mol, 2, 090 g/mol, 2,095 g/mol, 2,100 g/mol, 2,200 g/mol, 2,300 g/mol, 2,400 g/mol, 2,500 g/mol, 2,600 g/mol, 2,700 g/mol, 2,800 g/mol, 2,900 g/mol, 3,000 g/mol, 3,100 g/mol, 3,200 g/mol, 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol).

In some embodiments, the poloxamer has an average molar mass of polyoxypropylene subunits of greater than 2,250 g/mol (e.g., an average molar mass of polyoxypropylene subunits of about 2,300 g/mol, 2,400 g/mol, 2,500 g/mol, 2,600 g/mol, 2,700 g/mol, 2,800 g/mol, 2,900 g/mol, 3,000 g/mol, 3,100 g/mol, 3,200 g/mol, 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol).

In some embodiments, the poloxamer has an average molar mass of polyoxypropylene subunits of greater than 2,750 g/mol (e.g., an average molar mass of polyoxypropylene subunits of about 2,800 g/mol, 2,900 g/mol, 3,000 g/mol, 3,100 g/mol, 3,200 g/mol, 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol).

In some embodiments, the poloxamer has an average molar mass of polyoxypropylene subunits of greater than 3,250 g/mol (e.g., an average molar mass of polyoxypropylene subunits of about 3,300 g/mol, 3,400 g/mol, 3,500 g/mol, 3,600 g/mol, 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol).

In some embodiments, the poloxamer has an average molar mass of polyoxypropylene subunits of greater than 3,625 g/mol (e.g., an average molar mass of polyoxypropylene subunits of about 3,700 g/mol, 3,800 g/mol, 3,900 g/mol, 4,000 g/mol, 4,100 g/mol, 4,200 g/mol, 4,300 g/mol, 4,400 g/mol, 4,500 g/mol, 4,600 g/mol, 4,700 g/mol, 4,800 g/mol, 4,900 g/mol, or 5,000 g/mol).

In some embodiments, the poloxamer has an average molar mass of polyoxypropylene subunits of from about 2,050 g/mol to about 4,000 g/mol (e.g., about 2,050 g/mol, 2,055 g/mol, 2,060 g/mol, 2,065 g/mol, 2,070 g/mol, 2,075 g/mol, 2,080 g/mol, 2,085 g/mol, 2,090 g/mol, 2,095 g/mol, 2,100 g/mol, 2,105 g/mol, 2,110 g/mol, 2,115 g/mol, 2,120 g/mol, 2,125 g/mol, 2,130 g/mol, 2,135 g/mol, 2,140 g/mol, 2,145 g/mol, 2,150 g/mol, 2,155 g/mol, 2,160 g/mol, 2,165 g/mol, 2,170 g/mol, 2,175 g/mol, 2,180 g/mol, 2,185 g/mol, 2,190 g/mol, 2,195 g/mol, 2,200 g/mol, 2,205 g/mol, 2,210 g/mol, 2,215 g/mol, 2,220 g/mol, 2,225 g/mol, 2,230 g/mol, 2,235 g/mol, 2,240 g/mol, 2,245 g/mol, 2,250 g/mol, 2,255 g/mol, 2,260 g/mol, 2,265 g/mol, 2,270 g/mol, 2,275 g/mol, 2,280 g/mol, 2,285 g/mol, 2,290 g/mol, 2,295 g/mol, 2,300 g/mol, 2,305 g/mol, 2,310 g/mol, 2,315 g/mol, 2,320 g/mol, 2,325 g/mol, 2,330 g/mol, 2,335 g/mol, 2,340 g/mol, 2,345 g/mol, 2,350 g/mol, 2,355 g/mol, 2,360 g/mol, 2,365 g/mol, 2,370 g/mol, 2,375 g/mol, 2,380 g/mol, 2,385 g/mol, 2,390 g/mol, 2,395 g/mol, 2,400 g/mol, 2,405 g/mol, 2,410 g/mol, 2,415 g/mol, 2,420 g/mol, 2,425 g/mol, 2,430 g/mol, 2,435 g/mol, 2,440 g/mol, 2,445 g/mol, 2,450 g/mol, 2,455 g/mol, 2,460 g/mol, 2,465 g/mol, 2,470 g/mol, 2,475 g/mol, 2,480 g/mol, 2,485 g/mol, 2,490 g/mol, 2,495 g/mol, 2,500 g/mol, 2,505 g/mol, 2,510 g/mol, 2,515 g/mol, 2,520 g/mol, 2,525 g/mol, 2,530 g/mol, 2,535 g/mol, 2,540 g/mol, 2,545 g/mol, 2,550 g/mol, 2,555 g/mol, 2,560 g/mol, 2,565 g/mol, 2,570 g/mol, 2,575 g/mol, 2,580 g/mol, 2,585 g/mol, 2,590 g/mol, 2,595 g/mol, 2,600 g/mol, 2,605 g/mol, 2,610 g/mol, 2,615 g/mol, 2,620 g/mol, 2,625 g/mol, 2,630 g/mol, 2,635 g/mol, 2,640 g/mol, 2,645 g/mol, 2,650 g/mol, 2,655 g/mol, 2,660 g/mol, 2,665 g/mol, 2,670 g/mol, 2,675 g/mol, 2,680 g/mol, 2,685 g/mol, 2,690 g/mol, 2,695 g/mol, 2,700 g/mol, 2,705 g/mol, 2,710 g/mol, 2,715 g/mol, 2,720 g/mol, 2,725 g/mol, 2,730 g/mol, 2,735 g/mol, 2,740 g/mol, 2,745 g/mol, 2,750 g/mol, 2,755 g/mol, 2,760 g/mol, 2,765 g/mol, 2,770 g/mol, 2,775 g/mol, 2,780 g/mol, 2,785 g/mol, 2,790 g/mol, 2,795 g/mol, 2,800 g/mol, 2,805 g/mol, 2,810 g/mol, 2,815 g/mol, 2,820 g/mol, 2,825 g/mol, 2,830 g/mol, 2,835 g/mol, 2,840 g/mol, 2,845 g/mol, 2,850 g/mol, 2,855 g/mol, 2,860 g/mol, 2,865 g/mol, 2,870 g/mol, 2,875 g/mol, 2,880 g/mol, 2,885 g/mol, 2,890 g/mol, 2,895 g/mol, 2,900 g/mol, 2,905 g/mol, 2,910 g/mol, 2,915 g/mol, 2,920 g/mol, 2,925 g/mol, 2,930 g/mol, 2,935 g/mol, 2,940 g/mol, 2,945 g/mol, 2,950 g/mol, 2,955 g/mol, 2,960 g/mol, 2,965 g/mol, 2,970 g/mol, 2,975 g/mol, 2,980 g/mol, 2,985 g/mol, 2,990 g/mol, 2,995 g/mol, 3,000 g/mol, 3,005 g/mol, 3,010 g/mol, 3,015 g/mol, 3,020 g/mol, 3,025 g/mol, 3,030 g/mol, 3,035 g/mol, 3,040 g/mol, 3,045 g/mol, 3,050 g/mol, 3,055 g/mol, 3,060 g/mol, 3,065 g/mol, 3,070 g/mol, 3,075 g/mol, 3,080 g/mol, 3,085 g/mol, 3,090 g/mol, 3,095 g/mol, 3,100 g/mol, 3,105 g/mol, 3,110 g/mol, 3,115 g/mol, 3,120 g/mol, 3,125 g/mol, 3,130 g/mol, 3,135 g/mol, 3,140 g/mol, 3,145 g/mol, 3,150 g/mol, 3,155 g/mol, 3,160 g/mol, 3,165 g/mol, 3,170 g/mol, 3,175 g/mol, 3,180 g/mol, 3,185 g/mol, 3,190 g/mol, 3,195 g/mol, 3,200 g/mol, 3,205 g/mol, 3,210 g/mol, 3,215 g/mol, 3,220 g/mol, 3,225 g/mol, 3,230 g/mol, 3,235 g/mol, 3,240 g/mol, 3,245 g/mol, 3,250 g/mol, 3,255 g/mol, 3,260 g/mol, 3,265 g/mol, 3,270 g/mol, 3,275 g/mol, 3,280 g/mol, 3,285 g/mol, 3,290 g/mol, 3,295 g/mol, 3,300 g/mol, 3,305 g/mol, 3,310 g/mol, 3,315 g/mol, 3,320 g/mol, 3,325 g/mol, 3,330 g/mol, 3,335 g/mol, 3,340 g/mol, 3,345 g/mol, 3,350 g/mol, 3,355 g/mol, 3,360 g/mol, 3,365 g/mol, 3,370 g/mol, 3,375 g/mol, 3,380 g/mol, 3,385 g/mol, 3,390 g/mol, 3,395 g/mol, 3,400 g/mol, 3,405 g/mol, 3,410 g/mol, 3,415 g/mol, 3,420 g/mol, 3,425 g/mol, 3,430 g/mol, 3,435 g/mol, 3,440 g/mol, 3,445 g/mol, 3,450 g/mol, 3,455 g/mol, 3,460 g/mol, 3,465 g/mol, 3,470 g/mol, 3,475 g/mol, 3,480 g/mol, 3,485 g/mol, 3,490 g/mol, 3,495 g/mol, 3,500 g/mol, 3,505 g/mol, 3,510 g/mol, 3,515 g/mol, 3,520 g/mol, 3,525 g/mol, 3,530 g/mol, 3,535 g/mol, 3,540 g/mol, 3,545 g/mol, 3,550 g/mol, 3,555 g/mol, 3,560 g/mol, 3,565 g/mol, 3,570 g/mol, 3,575 g/mol, 3,580 g/mol, 3,585 g/mol, 3,590 g/mol, 3,595 g/mol, 3,600 g/mol, 3,605 g/mol, 3,610 g/mol, 3,615 g/mol, 3,620 g/mol, 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average molar mass of polyoxypropylene subunits of from about 2,750 g/mol to about 4,000 g/mol (e.g., about 2,750 g/mol, 2,755 g/mol, 2,760 g/mol, 2,765 g/mol, 2,770 g/mol, 2,775 g/mol, 2,780 g/mol, 2,785 g/mol, 2,790 g/mol, 2,795 g/mol, 2,800 g/mol, 2,805 g/mol, 2,810 g/mol, 2,815 g/mol, 2,820 g/mol, 2,825 g/mol, 2,830 g/mol, 2,835 g/mol, 2,840 g/mol, 2,845 g/mol, 2,850 g/mol, 2,855 g/mol, 2,860 g/mol, 2,865 g/mol, 2,870 g/mol, 2,875 g/mol, 2,880 g/mol, 2,885 g/mol, 2,890 g/mol, 2,895 g/mol, 2,900 g/mol, 2,905 g/mol, 2,910 g/mol, 2,915 g/mol, 2,920 g/mol, 2,925 g/mol, 2,930 g/mol, 2,935 g/mol, 2,940 g/mol, 2,945 g/mol, 2,950 g/mol, 2,955 g/mol, 2,960 g/mol, 2,965 g/mol, 2,970 g/mol, 2,975 g/mol, 2,980 g/mol, 2,985 g/mol, 2,990 g/mol, 2,995 g/mol, 3,000 g/mol, 3,005 g/mol, 3,010 g/mol, 3,015 g/mol, 3,020 g/mol, 3,025 g/mol, 3,030 g/mol, 3,035 g/mol, 3,040 g/mol, 3,045 g/mol, 3,050 g/mol, 3,055 g/mol, 3,060 g/mol, 3,065 g/mol, 3,070 g/mol, 3,075 g/mol, 3,080 g/mol, 3,085 g/mol, 3,090 g/mol, 3,095 g/mol, 3,100 g/mol, 3,105 g/mol, 3,110 g/mol, 3,115 g/mol, 3,120 g/mol, 3,125 g/mol, 3,130 g/mol, 3,135 g/mol, 3,140 g/mol, 3,145 g/mol, 3,150 g/mol, 3,155 g/mol, 3,160 g/mol, 3,165 g/mol, 3,170 g/mol, 3,175 g/mol, 3,180 g/mol, 3,185 g/mol, 3,190 g/mol, 3,195 g/mol, 3,200 g/mol, 3,205 g/mol, 3,210 g/mol, 3,215 g/mol, 3,220 g/mol, 3,225 g/mol, 3,230 g/mol, 3,235 g/mol, 3,240 g/mol, 3,245 g/mol, 3,250 g/mol, 3,255 g/mol, 3,260 g/mol, 3,265 g/mol, 3,270 g/mol, 3,275 g/mol, 3,280 g/mol, 3,285 g/mol, 3,290 g/mol, 3,295 g/mol, 3,300 g/mol, 3,305 g/mol, 3,310 g/mol, 3,315 g/mol, 3,320 g/mol, 3,325 g/mol, 3,330 g/mol, 3,335 g/mol, 3,340 g/mol, 3,345 g/mol, 3,350 g/mol, 3,355 g/mol, 3,360 g/mol, 3,365 g/mol, 3,370 g/mol, 3,375 g/mol, 3,380 g/mol, 3,385 g/mol, 3,390 g/mol, 3,395 g/mol, 3,400 g/mol, 3,405 g/mol, 3,410 g/mol, 3,415 g/mol, 3,420 g/mol, 3,425 g/mol, 3,430 g/mol, 3,435 g/mol, 3,440 g/mol, 3,445 g/mol, 3,450 g/mol, 3,455 g/mol, 3,460 g/mol, 3,465 g/mol, 3,470 g/mol, 3,475 g/mol, 3,480 g/mol, 3,485 g/mol, 3,490 g/mol, 3,495 g/mol, 3,500 g/mol, 3,505 g/mol, 3,510 g/mol, 3,515 g/mol, 3,520 g/mol, 3,525 g/mol, 3,530 g/mol, 3,535 g/mol, 3,540 g/mol, 3,545 g/mol, 3,550 g/mol, 3,555 g/mol, 3,560 g/mol, 3,565 g/mol, 3,570 g/mol, 3,575 g/mol, 3,580 g/mol, 3,585 g/mol, 3,590 g/mol, 3,595 g/mol, 3,600 g/mol, 3,605 g/mol, 3,610 g/mol, 3,615 g/mol, 3,620 g/mol, 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average molar mass of polyoxypropylene subunits of from about 3,250 g/mol to about 4,000 g/mol (e.g., about 3,250 g/mol, 3,255 g/mol, 3,260 g/mol, 3,265 g/mol, 3,270 g/mol, 3,275 g/mol, 3,280 g/mol, 3,285 g/mol, 3,290 g/mol, 3,295 g/mol, 3,300 g/mol, 3,305 g/mol, 3,310 g/mol, 3,315 g/mol, 3,320 g/mol, 3,325 g/mol, 3,330 g/mol, 3,335 g/mol, 3,340 g/mol, 3,345 g/mol, 3,350 g/mol, 3,355 g/mol, 3,360 g/mol, 3,365 g/mol, 3,370 g/mol, 3,375 g/mol, 3,380 g/mol, 3,385 g/mol, 3,390 g/mol, 3,395 g/mol, 3,400 g/mol, 3,405 g/mol, 3,410 g/mol, 3,415 g/mol, 3,420 g/mol, 3,425 g/mol, 3,430 g/mol, 3,435 g/mol, 3,440 g/mol, 3,445 g/mol, 3,450 g/mol, 3,455 g/mol, 3,460 g/mol, 3,465 g/mol, 3,470 g/mol, 3,475 g/mol, 3,480 g/mol, 3,485 g/mol, 3,490 g/mol, 3,495 g/mol, 3,500 g/mol, 3,505 g/mol, 3,510 g/mol, 3,515 g/mol, 3,520 g/mol, 3,525 g/mol, 3,530 g/mol, 3,535 g/mol, 3,540 g/mol, 3,545 g/mol, 3,550 g/mol, 3,555 g/mol, 3,560 g/mol, 3,565 g/mol, 3,570 g/mol, 3,575 g/mol, 3,580 g/mol, 3,585 g/mol, 3,590 g/mol, 3,595 g/mol, 3,600 g/mol, 3,605 g/mol, 3,610 g/mol, 3,615 g/mol, 3,620 g/mol, 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 g/mol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 g/mol).

In some embodiments, the poloxamer has an average molar mass of polyoxypropylene subunits of from about 3,625 g/mol to about 4,000 g/mol (e.g., about 3,625 g/mol, 3,630 g/mol, 3,635 g/mol, 3,640 g/mol, 3,645 g/mol, 3,650 g/mol, 3,655 g/mol, 3,660 g/mol, 3,665 g/mol, 3,670 g/mol, 3,675 g/mol, 3,680 g/mol, 3,685 g/mol, 3,690 g/mol, 3,695 g/mol, 3,700 g/mol, 3,705 g/mol, 3,710 g/mol, 3,715 g/mol, 3,720 g/mol, 3,725 g/mol, 3,730 g/mol, 3,735 g/mol, 3,740 g/mol, 3,745 g/mol, 3,750 g/mol, 3,755 g/mol, 3,760 g/mol, 3,765 g/mol, 3,770 g/mol, 3,775 g/mol, 3,780 g/mol, 3,785 g/mol, 3,790 g/mol, 3,795 g/mol, 3,800 g/mol, 3,805 g/mol, 3,810 g/mol, 3,815 g/mol, 3,820 g/mol, 3,825 g/mol, 3,830 g/mol, 3,835 g/mol, 3,840 g/mol, 3,845 g/mol, 3,850 g/mol, 3,855 g/mol, 3,860 g/mol, 3,865 g/mol, 3,870 g/mol, 3,875 g/mol, 3,880 g/mol, 3,885 g/mol, 3,890 g/mol, 3,895 g/mol, 3,900 g/mol, 3,905 g/mol, 3,910 glmol, 3,915 g/mol, 3,920 g/mol, 3,925 g/mol, 3,930 g/mol, 3,935 g/mol, 3,940 g/mol, 3,945 g/mol, 3,950 g/mol, 3,955 g/mol, 3,960 g/mol, 3,965 g/mol, 3,970 g/mol, 3,975 g/mol, 3,980 g/mol, 3,985 g/mol, 3,990 g/mol, 3,995 g/mol, or 4,000 glmol).

In some embodiments, the poloxamer has an average ethylene oxide content of greater than 40% by mass (e.g., about 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of greater than 50% by mass (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of greater than 60% by mass (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of greater than 70% by mass (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or more).

In some embodiments, the poloxamer has an average ethylene oxide content of from about 40% to about 90% (e.g., about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90%).

In some embodiments, the poloxamer has an average ethylene oxide content of from about 50% to about 85% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, or 85%).

In some embodiments, the poloxamer has an average ethylene oxide content of from about 60% to about 80% (e.g., about 60%, 61%, 62%, 63%, 64%, 65%, 66%, 67%, 68%, 69%, 70%, 71%, 72%, 73%, 74%, 75%, 76%, 77%, 78%, 79%, 80%).

In some embodiments, the poloxamer has an average molar mass of greater than 10,000 g/mol (e.g., about 10,100 g/mol, 10,200 g/mol, 10,300 g/mol, 10,400 g/mol, 10,500 g/mol, 10,600 g/mol, 10,700 g/mol, 10,800 g/mol, 10,900 g/mol, 11,000 g/mol, 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of greater than 11,000 g/mol (e.g., about 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of greater than 12,000 g/mol (e.g., about 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of greater than 12,500 g/mol (e.g., about 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 10,000 g/mol to about 15,000 g/mol (e.g., about 10,000 g/mol, 10,100 g/mol, 10,200 g/mol, 10,300 g/mol, 10,400 g/mol, 10,500 g/mol, 10,600 g/mol, 10,700 g/mol, 10,800 g/mol, 10,900 g/mol, 11,000 g/mol, 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 11,000 g/mol to about 15,000 g/mol (e.g., about 11,000 g/mol, 11,100 g/mol, 11,200 g/mol, 11,300 g/mol, 11,400 g/mol, 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 11,500 g/mol to about 15,000 g/mol (e.g., about 11,500 g/mol, 11,600 g/mol, 11,700 g/mol, 11,800 g/mol, 11,900 g/mol, 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 12,000 g/mol to about 15,000 g/mol (e.g., about 12,000 g/mol, 12,100 g/mol, 12,200 g/mol, 12,300 g/mol, 12,400 g/mol, 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

In some embodiments, the poloxamer has an average molar mass of from about 12,500 g/mol to about 15,000 g/mol (e.g., about 12,500 g/mol, 12,600 g/mol, 12,700 g/mol, 12,800 g/mol, 12,900 g/mol, 13,000 g/mol, 13,100 g/mol, 13,200 g/mol, 13,300 g/mol, 13,400 g/mol, 13,500 g/mol, 13,600 g/mol, 13,700 g/mol, 13,800 g/mol, 13,900 g/mol, 14,000 g/mol, 14,100 g/mol, 14,200 g/mol, 14,300 g/mol, 14,400 g/mol, 14,500 g/mol, 14,600 g/mol, 14,700 g/mol, 14,800 g/mol, 14,900 g/mol, or 15,000 g/mol).

Poloxamers P288, P335, P338, and P407

Poloxamers that may be used in conjunction with the compositions and methods of the disclosure include "poloxamer 288" (also referred to in the art as "P288" and poloxamer "F98") having the approximate chemical formula $HO(C_2H_4O)_x(C_3H_6O)_y(C_2H_4O)_zH$, wherein the sum of x and y is about 236.36, and z is about 44.83. The average molecular weight of P288 is about 13,000 g/mol.

In some embodiments, the poloxamer is a variant of P288, such as a variant of the formula $HO(C_2H_4O)_x(C_3H_6O)_y(C_2H_4O)_zH$, wherein the sum of x and y is from about 220 to about 250, and z is from about 40 to about 50. In some embodiments, the average molecular weight of the poloxamer is from about 12,000 g/mol to about 14,000 g/mol.

Poloxamers that may be used in conjunction with the compositions and methods of the disclosure further include "poloxamer 335" (also referred to in the art as "P335" and poloxamer "P105"), having the approximate chemical formula $HO(C_2H_4O)_x(C_3H_6O)_y(C_2H_4O)_zH$, wherein the sum of x and y is about 73.86, and z is about 56.03. The average molecular weight of P335 is about 6,500 g/mol.

In some embodiments, the poloxamer is a variant of P335, such as a variant of the formula $HO(C_2H_4O)_x(C_3H_6O)_y(C_2H_4O)_zH$, wherein the sum of x and y is from about 60 to about 80, and z is from about 50 to about 60. In some embodiments, the average molecular weight of the poloxamer is from about 6,000 g/mol to about 7,000 g/mol.

Poloxamers that may be used in conjunction with the compositions and methods of the disclosure further include "poloxamer 338" (also referred to in the art as "P338" and poloxamer "F108"), having the approximate chemical formula $HO(C_2H_4O)_x(C_3H_6O)_y(C_2H_4O)_zH$, wherein the sum of x and y is about 265.45, and z is about 50.34. The average molecular weight of P335 is about 14,600 g/mol.

In some embodiments, the poloxamer is a variant of P338, such as a variant of the formula $HO(C_2H_4O)_x(C_3H_6O)_y(C_2H_4O)_zH$, wherein the sum of x and y is from about 260 to about 270, and z is from about 45 to about 55. In some embodiments, the average molecular weight of the poloxamer is from about 14,000 g/mol to about 15,000 g/mol.

Poloxamers that may be used in conjunction with the compositions and methods of the disclosure further include "poloxamer 407" (also referred to in the art as "P407" and poloxamer "F127"), having the approximate chemical formula $HO(C_2H_4O)_x(C_3H_6O)_y(C_2H_4O)_zH$, wherein the sum of x and y is about 200.45, and z is about 65.17. The average molecular weight is about 12,600 g/mol.

In some embodiments, the poloxamer is a variant of P407, such as a variant of the formula $HO(C_2H_4O)_x(C_3H_6O)_y(C_2H_4O)_zH$, wherein the sum of x and y is from about 190 to about 210, and z is from about 60 to about 70. In some embodiments, the average molecular weight of the poloxamer is from about 12,000 g/mol to about 13,000 g/mol.

For clarity, the terms "average molar mass" and "average molecular weight" are used interchangeable herein to refer to the same quantity. The average molar mass, ethylene oxide content, and propylene oxide content of a poloxamer, as described herein, can be determined using methods disclosed in Alexandridis and Hatton, Colloids and Surfaces A: Physicochemical and Engineering Aspects 96:1-46 (1995), the disclosure of which is incorporated herein by reference in its entirety.

Sterols

The lipid-polymer composite particles described herein may further include one or more sterols. Sterols are lipids that are often found naturally in plants, animals, and fungi. Phytosterols refers to a class of plant sterol molecules, which are naturally occurring compounds found in plant cell membranes. Phytosterols include both plant sterols and stanols. Phytosterols may be derived from any common plant source, such as soy, wood, tall oil, vegetable oil, and the like. Phytosterols include β-sitosterol, campesterol, stigmasterol, stigmastanol, campestanol, brassicasterol, ergosterol, lupeol, cycloartenol, and the like. The sterol as described herein may be any cholesterol or derivative thereof that alters the fluidity of a lipid layer. The sterol may be a naturally occurring sterol, e.g., a sterol derived or found in a natural source. Alternatively, the sterol may be a synthetic sterol, e.g., a sterol analog or derivative that is not naturally existing. In some preferred embodiments, the sterol is cholesterol or an analog thereof (e.g., thiocholesterol, epicholesterol, β-sitosterol (Si-Lip), stigmasterol (St-Lip), or lanosterol (La-Lip)). The concentration of the sterol in the compositions described herein may be, e.g., from about 1% to about 50% (e.g., from about 5% to about 45%, from about 10% to about 40%) of total lipid composition.

The sterol and phospholipid may be present in the particles in a weight ratio of, e.g., from about 0.01 to about 0.5 sterol:phospholipid. For example, the weight ratio of sterol:phospholipid may be, e.g., from about 0.01 to about 0.1, from about 0.1 to about 0.2, from about 0.2 to about 0.3, from about 0.3 to about 0.4, from about 0.4 to about 0.5, from about 0.01 to about 0.2, from about 0.01 to about 0.3, from about 0.01 to about 0.4, from about 0.1 to about 0.15, from about 0.1 to about 0.25. For example, the weight ratio of sterol:phospholipid may be about 0.01, 0.02, 0.03, 0.04, 0.05, 0.06, 0.07, 0.08, 0.09, 0.1, 0.15, 0.2, 0.25, 0.3, 0.35, 0.4, 0.45, or 0.5.

Sterols also encompasses esterified derivatives thereof, sometimes referred to as sterol esters or stanol esters. Sterol esters are sterols esterified with a fatty acid, such as a long chain (e.g., $C_6$-$C_{24}$, e.g., $C_{10}$-$C_{24}$, e.g., $C_{14}$-$C_{24}$) fatty acid, such as octanoic acid, decanoic acid, undecanoic acid, lauric acid, myristic acid, palmitic acid, stearic acid, oleic acid, linoleic acid, and linolenic acid. Sterols and their esters may be fully saturated (e.g., hydrogenated). Pharmaceutical compositions containing sterols or their esters may include one or more of the foregoing components or a mixture thereof.

Bioactive Agents

The lipid-polymer composite particles described herein may encapsulate a bioactive agent. Bioactive agents may include a therapeutic agent, a nutraceutical agent, or a recreational agent. In some embodiments, the bioactive agent is a cannabinoid or a cannabinoid derivative. In more preferred embodiments, the cannabinoid or derivative thereof is one or more of cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid-C4 (THCA-C4), delta-9-tetrahydrocannabinol-C4 (THC-C4), delta-9-tetrahydrocannabivarinic acid (THCVA), delta-9-tetrahydrocannabivarin (THCV), delta-9-tetrahydrocannabiorcolic acid (THCA-C1), delta-9-tetrahydrocannabiorcol (THC-C1), delta-7-cis-iso-tetrahydrocannabivarin, delta-8-tetrahydrocannabinolic acid ($\Delta^8$-THCA), delta-8-tetrahydrocannabinol THC), cannabicyclolic acid (CBLA), cannabicyclol (CBL), cannabicyclovarin (CBLV), cannnabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-C4 (CBN-C4), cannabivarin (CBV), cannabinol-C2 (CBN-C2), cannabiorcol (CBN-C1), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxy-alpha-alpha-2-trimethyl-9-n-propyl-2,6-metha- no-2H-1-benzoxocin-5-methanol (OH-iso-HHCV), cannabiripsol (CBR) and trihydroxy-delta-9-tetrahydrocannabinol (triOH-THC). In some embodiments, the cannabinoid derivatives are naturally occurring. In some embodiments, the cannabinoid derivatives are non-naturally-occurring, including those that are chemically or enzymatically synthesized. In some embodiments, the bioactive agent is a terpene, a flavonoid, an antibiotic, an antiseptic agent, an antifungal, an antibacterial, an analgesic, an anti-inflammatory agent, an antiprotozoal agent, a steroid, an antiviral agent, a lipophilic drug (e.g., solubility less than 1 mg/ml), an anti-VEGF agent, an anti-glaucoma agent, an essential oil, nicotine or a nicotine analogue, cyclosporin A, tacrolimus, isotretinoin, propofol, griseofulvin or any combination thereof.

In some embodiments, the bioactive agent includes an immunogen (e.g., a vaccine component, e.g., a DNA vaccine, an RNA vaccine, or a polypeptide vaccine). The immunogen may be, for example, a polypeptide or a fragment, variant, or analog thereof, a nucleic acid (e.g., DNA or RNA), or another component of a cell. In some embodiments, the invention features a vaccine that includes a composition as described herein.

In some embodiments, the essential oil includes tea tree oil, myrrh oil, eucalyptus oil, clove oil, lavender oil, peppermint oil, chamomile oil, Roman chamomile oil, German chamomile oil, frankincense oil, helichrysum oil, cypress oil, angelica oil, labdanum oil, petitgrain bigarade oil, orange bigarade oil, bergamot oil, sweet orange oil, palmarosa oil, lemon-scented ironbark oil, may chang oil, basil oil, sweet marjoram oil, geranium oil, patchouli oil, valerian oil, sandalwood oil, neroli bigarade oil, grapefruit oil, coriander oil, citronella oil, black peppermint oil, gully gum oil, juniper twig oil, spearmint oil, scots pine oil, rosemary oil, clary oil, ginger oil, lemon oil, mandarin oil, cumin oil, juniper berry oil, lemon balm oil, myrtle oil, Ravensara oil, sweet thyme oil, everlasting oil, manuka oil, dwarf pine oil, oregano oil, vetiver oil, Melissa oil, white fir oil, cassia oil, lemongrass oil, lime oil, wintergreen oil, fennel oil, ylang ylang oil, or a combination thereof.

In some embodiments, the weight ratio between the poloxamer and the bioactive agent is from about 4 to about 8 (e.g., from about 4.1 to about 7.9, or from about 4.2 to about 7.8, from about 4.3 to about 7.7, from about 4.4 to about 7.6, from about 4.5 to about 7.5, from about 4.6 to about 7.4, from about 4.7 to about 7.3, from about 4.8 to about 7.2, from about 4.9 to about 7.1, from about 5.0 to about 7.0, from about 5.1 to about 6.9, from about 5.2 to about 6.8, from about 5.3 to about 6.7, from about 5.4 to about 6.6, from about 5.5 to about 6.5, from about 5.6 to about 6.4, from about 5.7 to about 6.3, from about 5.8 to about 6.2, or from about 5.9 to about 6.1). In some embodiments the bioactive agent (e.g., cannabinoid or a derivative thereof) is present in the formulation at a concentration from about 0.01% to about 10% (e.g., from about 0.05% to about 9.5%, from about 0.1% to about 9%, from about 0.2% to about 8.5%, from about 0.4% to about 8%, from about 0.5% to about 7.5%, from about 1% to about 7%, from about 1.5% to about 6.5%, from about 2% to about 6%, from about 2.5% to about 5.5%, from about 3% to about 5%, from about 3.5% to about 4.5%, from about 4% to about 4.49%, e.g., about 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, 0.30%, 0.31%, 0.32%, 0.33%, 0.34%, 0.35%, 0.36%, 0.37%, 0.38%, 0.39%, 0.40%, 0.41%, 0.42%, 0.43%, 0.44%, 0.45%, 0.46%, 0.47%, 0.48%, 0.49%, 0.50%, 0.60%, 0.61%, 0.62%, 0.63%, 0.64%, 0.65%, 0.66%, 0.67%, 0.68%, 0.69%, 0.70%, 0.71%, 0.72%, 0.73%, 0.74%, 0.75%, 0.76%, 0.77%, 0.78%, 0.79%, 0.80%, 0.81%, 0.82%, 0.83%, 0.84%, 0.85%, 0.86%, 0.87%, 0.88%, 0.89%, 0.90%, 0.91%, 0.92%, 0.93%, 0.94%, 0.95%, 0.96%, 0.97%, 0.98%, 0.99%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 0110.0%) by weight of the composition. In some embodiments, the bioactive agent (e.g., an essential oil) is present in the formulation at a concentration from about 0.01% to about 95% (e.g., about 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, 0.30%, 0.31%, 0.32%, 0.33%, 0.34%, 0.35%, 0.36%, 0.37%, 0.38%, 0.39%, 0.40%, 0.41%, 0.42%, 0.43%, 0.44%, 0.45%, 0.46%, 0.47%, 0.48%, 0.49%, 0.50%, 0.60%, 0.61%, 0.62%, 0.63%, 0.64%, 0.65%, 0.66%, 0.67%, 0.68%, 0.69%, 0.70%, 0.71%, 0.72%, 0.73%, 0.74%, 0.75%, 0.76%, 0.77%, 0.78%, 0.79%, 0.80%, 0.81%, 0.82%, 0.83%, 0.84%, 0.85%, 0.86%, 0.87%, 0.88%, 0.89%, 0.90%, 0.91%, 0.92%, 0.93%, 0.94%, 0.95%, 0.96%, 0.97%, 0.98%, 0.99%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95%) by weight of the composition.

The bioactive agent encapsulated by the lipid-polymer composite particles described herein may also be a terpene, a flavonoid, an antibiotic, an antiseptic agent, an antifungal, an antibacterial, an analgesic, an anti-inflammatory agent, an antiprotozoal agent, a steroid, an antiviral agent, a lipophilic drug, an anti-VEGF agent, or an anti-glaucoma agent. In some embodiments, the terpene is myrcene, beta-caryophyllene, linalool, alpha pinene, beta pinene, ocimene, terpinolene, ocimene, terpinolene, alpha tepinol, alpha terpinene, gamma terpinene, alpha phellandrene, cymene, camphene, delta-3-carene, fenchol, 1,8-cineole, nerolidol, borneol, eucalyptol, camphene, or limonene. In some embodiments, the flavonoid is selected from the group consisting of cannaflavin A, cannaflavin B, phenolic acids, stilbenoids, phytochemicals, dihydroflavonols, anthocyanins, anthocyanidins, polyphenols, tannins, flavones, flavonols, flavan-3-ols, flavan-4-ol, flavan-3,4-diol, homoisoflavonoids, phenylpropanoids, phloroglucinols, coumarins, phenolic acids, naphthodianthrones, steroid glycosides, bioflavonoids, or isoflavonoids.

In some embodiments, the bioactive agent is a vaccine component, e.g., a protein or polypeptide fragment that induces immunity, prevents an infectious disease, and/or reduces the risk of an infectious disease.

In some embodiments, the bioactive compound is nicotine, a nicotine analogue or a nicotine derivative. In other embodiments, the bioactive agent is cyclosporin A, tacrolimus, isotretinoin, propofol, griseofulvin, azithromycin, or a non-steroidal anti-inflammatory drug (NSAID).

Pharmaceutical Compositions

The compositions described herein are preferably formulated into pharmaceutical compositions for administration to human subjects in a biologically compatible form suitable for administration in vivo. The pharmaceutical composition can be formulated with a pharmaceutically acceptable carrier or excipient. A pharmaceutically acceptable carrier or excipient refers to a carrier (e.g., carrier, media, diluent, solvent, vehicle, etc.) which does not significantly interfere with the biological activity or effectiveness of the active ingredient(s) of a pharmaceutical composition and which is not excessively toxic to the host at the concentrations at which it is used or administered. Other pharmaceutically acceptable ingredients can be present in the composition as well. Suitable substances and their use for the formulation of pharmaceutically active compounds are well-known in the art (see, for example, Remington: The Science and Practice of Pharmacy. 21st Edition. Philadelphia, PA. Lippincott Williams & Wilkins, 2005, for additional discussion of pharmaceutically acceptable substances and methods of preparing pharmaceutical compositions of various types).

A pharmaceutical composition is typically formulated to be compatible with its intended route of administration. For oral administration, agents can be formulated by combining the bioactive agent with pharmaceutically acceptable carriers well known in the art. Such carriers enable the agents of the invention to be formulated as a powder, tablet, pill, capsule, lozenge, liquid, gel, syrup, slurry, suspension, and the like. It is recognized that some pharmaceutical compositions, if administered orally, must be protected from digestion. This is typically accomplished either by complexing the protein with a composition to render it resistant to acidic and enzymatic hydrolysis or by packaging the protein in an appropriately resistant carrier such as a liposome. Suitable excipients for oral dosage forms include, for example, fillers such as sugars, including lactose, sucrose, mannitol, or sorbitol; cellulose preparations such as, for example, starch, gelatin, gum tragacanth, methyl cellulose, hydroxypropylmethyl cellulose, sodium carboxymethylcellulose, and/or polyvinylpyrrolidone (PVP). Disintegrating agents may be added, for example, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

For administration by inhalation, pharmaceutical compositions may be formulated in the form of an aerosol spray from a pressured container or dispenser, which contains a suitable propellant, e.g., a gas such as carbon dioxide, a fluorocarbon, or a nebulizer. Liquid or dry aerosol (e.g., dry powders, large porous particles, etc.) can also be used. For topical application, a pharmaceutical composition may be formulated in a suitable ointment, lotion, gel, or cream containing the active components suspended or dissolved in one or more pharmaceutically acceptable carriers suitable for use in such compositions. Compositions formulated for ocular administration may be formulated, e.g., with hyaluronic acid.

The compositions described herein may be administered to a subject in a variety of forms depending on the selected route of administration, as will be understood by those skilled in the art. The compositions described herein may be administered, for example, by any route that allows the composition (e.g., lipid-polymer composite particle, e.g., micelle or LNP) to reach the target cells. The composition may be administered, for example, by oral, topical, parenteral, intrathecal, intracerebroventricular, intraparenchymal, buccal, sublingual, nasal, rectal, patch, pump, transdermal, sublingual, vaginal, ocular, otic, or nasal administration and the pharmaceutical compositions formulated accordingly. The composition may be administered via inhalation or nebulization. Parenteral administration includes intravenous, intraperitoneal, subcutaneous, intramuscular, transepithelial, nasal, intrapulmonary, rectal, and topical modes of administration. sublingually, buccally, rectally, vaginally, by ocular route, otic route, or nasal route.

In some embodiments, the compositions described herein are formulated as part of a food conveyance, e.g., that can be administered as a food or with a meal.

In some embodiments, the compositions described herein include one or more essential oils, e.g., tea tree oil, myrrh oil, eucalyptus oil, clove oil, lavender oil, peppermint oil, Roman chamomile oil, German chamomile oil, frankincense oil, helichrysum oil, cypress oil, angelica oil, labdanum oil, petitgrain bigarade oil, orange bigarade oil, bergamot oil, sweet orange oil, palmarosa oil, lemon-scented ironbark oil, may chang oil, basil oil, sweet marjoram oil, geranium oil, patchouli oil, valerian oil, sandalwood oil, neroli bigarade oil, grapefruit oil, coriander oil, citronella oil, black peppermint oil, gully gum oil, juniper twig oil, spearmint oil, scots pine oil, rosemary oil, clary oil, ginger oil, lemon oil, mandarin oil, cumin oil, juniper berry oil, lemon balm oil, myrtle oil, Ravensara oil, sweet thyme oil, everlasting oil, manuka oil, dwarf pine oil, oregano oil, vetiver oil, Melissa oil, white fir oil, cassia oil, lemongrass oil, lime oil, wintergreen oil, fennel oil, ylang ylang oil, or a combination thereof. In some embodiments, the compositions include a plurality of essential oils (e.g., 2, 3, 4, 5, 6, 7, 8, 9, or 10 essential oils). In some embodiments, the concentration of essential oil in the composition is 0.01% to 95% by weight (e.g., 5%, 10%, 15%, 20%, 25%, 30%, 35%, 40%, 45%, 50%, 55%, 60%, 65%, 70%, 75%, 80%, 85%, 90%, or 95%) of the composition.

In some embodiments, the compositions described herein are formulated as eye drops. In some embodiments, the eye drops contain one or more of the essential oils, e.g., 0.01% to 95% by weight (e.g., 5%, 10%, 15%, 20%, 25%, 30%, 35%, 40%, 45%, 50%, 55%, 60%, 65%, 70%, 75%, 80%, 85%, 90%, or 95%) of the composition.

In general, the dosage of a pharmaceutical composition (e.g., of the bioactive agent) may be in the range of from about 1 ng to about 1 g (e.g., from about 1 ng to about 10 ng, e.g., 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., from about 100 ng to about 1 μg, e.g., 200 ng, 300 ng, 400 ng, 500 ng, 600 ng, 700 ng, 800 ng, 900 ng, 1 μg, e.g., from about 1 μg to about 10 μg, e.g., 1 μg, 2 μg, 3 μg, 4 μg, 5 μg, 6 μg, 7 μg, 8 μg, 9 μg, 10 μg, e.g., from about 10 μg to about 100 μg, e.g., 20 μg, 30 μg, 40 μg, 50 μg, 60 μg, 70 μg, 80 μg, 90 μg, 100 μg, e.g., 100 μg — 1 mg, e.g., 200 μg, 300 μg, 400 μg, 500 μg, 600 μg, 700 μg, 800 μg, 900 μg, 1 mg, e.g., from about 1 mg to about 10 mg, e.g., 2 mg, 3 mg, 4 mg, 5 mg, 6 mg, 7 mg, 8 mg, 9 mg, 10 mg, e.g., from about 10 mg to about 100 mg, e.g., 20 mg, 30 mg, 40 mg, 50 mg, 60 mg, 70 mg, 80 mg, 90 mg, 100 mg, e.g., from about 100 mg to about 1 g, e.g., 200 mg, 300 mg, 400 mg, 500 mg, 600 mg, 700 mg, 800 mg, 900 mg, or 1 g).

The dosage of the pharmaceutical composition (e.g., of the bioactive agent) may be administered per kg of bodyweight of the subject. For example, the dosage may be from about 0.01 mg/kg to about 100 mg/kg, e.g., about 0.01 mg/kg to about 30 mg/kg, e.g., from about 0.01 mg/kg to about 10 mg/kg, from about 0.1 mg/kg to about 1 mg/kg, e.g., about 0.02 mg/kg, 0.03 mg/kg, 0.03 mg/g, 0.04 mg/kg, 0.05 mg/kg, 0.06 mg/kg, 0.07 mg/kg, 0.08 mg/kg, 0.08 mg/kg, 0.09 mg/kg, 0.1 mg/kg, 0.2 mg/kg, 0.3 mg/kg 0.4 mg/kg, 0.4 mg/kg, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 65 mg/kg, 70 mg/kg, 75 mg/kg, 80 mg/kg, 85 mg/kg, 90 mg/kg, 95 mg/kg, or 100 mg/kg. The foregoing dosages may be administered once per day, week, month, or year.

The dosage of the compositions (e.g., a composition including a bioactive agent) described herein, can vary depending on many factors, such as the pharmacodynamic properties of the agent, the mode of administration, the age, health, and weight of the recipient, the nature and extent of the symptoms, the frequency of the treatment, and the type of concurrent treatment, if any, and the clearance rate of the composition in the animal to be treated. The compositions described herein may be administered initially in a suitable dosage that may be adjusted as required, depending on the clinical response. In some embodiments, the dosage of a composition (e.g., a composition including a bioactive agent) is a prophylactically or a therapeutically effective amount. Furthermore, it is understood that all dosages may be continuously given or divided into dosages given per a given time frame. The composition can be administered, for example, every hour, day, week, month, or year. In some embodiments, the composition may be administered continuously or systemically.

The compositions described herein may be prepared using a multi-step process. In some embodiments, the sequence of steps in the process provide optimal particle size, polydispersity, solution transparency, pH, tonicity, size distribution, stability, and loading of the bioactive agent. In some embodiments, the bioactive agent is homogenized with the polymer in a first step, e.g., at a temperature of from about 50° C. to about 70° C., e.g., about 60° C. In a second step, a solution containing a lipid and a sterol is added to the homogenized bioactive and polymer suspension using an immersed injection (e.g., ethanol injection).

Methods of Use

The compositions herein described are formulated to treat a disease or condition (e.g., an eye condition, e.g., inflammation, eye pain, pink eye, dark eye circles, red eye, bacterial eye infection, fungal eye infection, viral eye infection, swelling, neovascularization, a nutrient deficiency, macular degeneration, glaucoma, or elevated eye pressure, pain, a bacterial infection, a fungal infection, a protozoal infection, anxiety, agitation, stress, fatigue, insomnia, mental exhaustion, memory loss, organ rejection, eczema, acne, and a skin infection). In some embodiments, the compositions are used for supplementing nutrition. In some embodiments, the compositions are used for recreational purposes.

The compositions herein described can be formulated as eye drops to treat an eye condition such as dry eye disease, inflammation, eye pain, pink eye, dark eye circles, red eye, bacterial eye infection, fungal eye infection, viral eye infection, a nutrient deficiency, macular degeneration, glaucoma, or elevated eye pressure.

In some embodiments, the compositions can be used to treat a disease or condition selected from inflammation, pain, a bacterial infection, a fungal infection, a protozoal infection, anxiety, agitation, stress, fatigue, insomnia, mental exhaustion, memory loss, organ rejection, eczema, acne, and a skin infection (e.g., athlete's foot, ring worm, or jock itch).

In some embodiments, the compositions described herein can be administered to a subject as an immunogenic composition (e.g., a vaccine). The bioactive agent may include an immunogen (e.g., a vaccine component, e.g., a DNA vaccine, an RNA vaccine, or a polypeptide vaccine). The immunogen may be, for example, a polypeptide or a fragment, variant, or analog thereof, a nucleic acid (e.g., DNA or RNA), or another component of a cell. The composition may be administered to a subject to prevent the onset of a disease or condition or to reduce the risk of acquiring a disease or condition. The immunogenic composition may be administered, for example, topically, orally, by injection, sublingually, buccally, rectally, vaginally, by ocular route, by otic route, by nasal route, by inhalation, by nebulization, or transdermally. In some embodiments, the immunogenic composition is administered intravenously, subcutaneously, or intramuscularly, The compositions may be administered to the eye of a subject, to a region surrounding the eye of the subject, to an exterior region of the eye, to an eyelid (e.g., to an exterior region of an eyelid, to an interior region of an eyelid), or to a lacrimal duct.

The compositions can be administered as eye drops (e.g., 1, 2, 3, 4, 5, 6, 7, 8, 9, or 10 eye drops per day) on each affected eye.

In some embodiments, the compositions can be administered to a subject for recreational use. The composition may be administered, e.g., orally, inhaled, parenterally, or topically to the subject for recreational use when desired.

The compositions can be administered once a day, twice a day, three times a day, four times a day, five times a day, six times a day, seven times a day, eight times a day, nine times a day, ten times a day, eleven times a day, twelve times a day, thirteen times a day, fourteen times a day, fifteen times a day, sixteen times a day, eighteen times a day, nineteen times a day, twenty times a day, twenty-one times a day, twenty-two times a day, twenty-three times a day, or twenty-four times a day. The compositions can also be administered weekly, biweekly, monthly, or bimonthly. The compositions can be administered before sleep or after sleep.

In some embodiments, the compositions are administered to a subject topically, orally, by injection, sublingually, buccally, rectally, vaginally, by ocular route, by otic route, by nasal route, by inhalation, by nebulization, or transdermally.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Preparation of Phospholipid Preliminary Liposomes

Preparation and visual characterization of phospholipid liposomal compositions was performed. Three variant formulations, Fa1, Fa2, and Fa3 were prepared using 1,2-distearoyl-sn-glycero-3-phosphocholine (DSPC), cannabidiol (CBD) and optionally cholesterol. Fa1, was prepared by mixing DSPC (1 mg/ml), CBD (30 mg/ml), and cholesterol (0.37 mg/ml) in ethanol, followed by injection into DI water (Table 1). Fa2, was prepared by mixing DSPC (1 mg/ml), and CBD (30 mg/ml) in ethanol and injecting it into DI water. Fa3, was prepared by mixing DSPC (2 mg/ml), CBD (30 mg/ml), and cholesterol (0.73 mg/ml) in ethanol followed by injection into DI water.

TABLE 1

Preliminary liposomal formulations Fa.

| Formulation No. | Formulation Contents | Method |
|---|---|---|
| Fa1 | DSPC 1 mg/ml, CBD 30 mg/ml and Chol 0.37 mg/ml (15 molar % of DSPC) | Ethanol Injection |

TABLE 1-continued

| Preliminary liposomal formulations Fa. | | |
|---|---|---|
| Formulation No. | Formulation Contents | Method |
| Fa2 | DSPC 1 mg/ml, CBD 30 mg/ml | Ethanol Injection |
| Fa3 | DSPC 2 mg/ml, CBD 30 mg/ml and Chol 0.73 mg/ml (15 molar % of DSPC) | Ethanol Injection |

Figure 1:
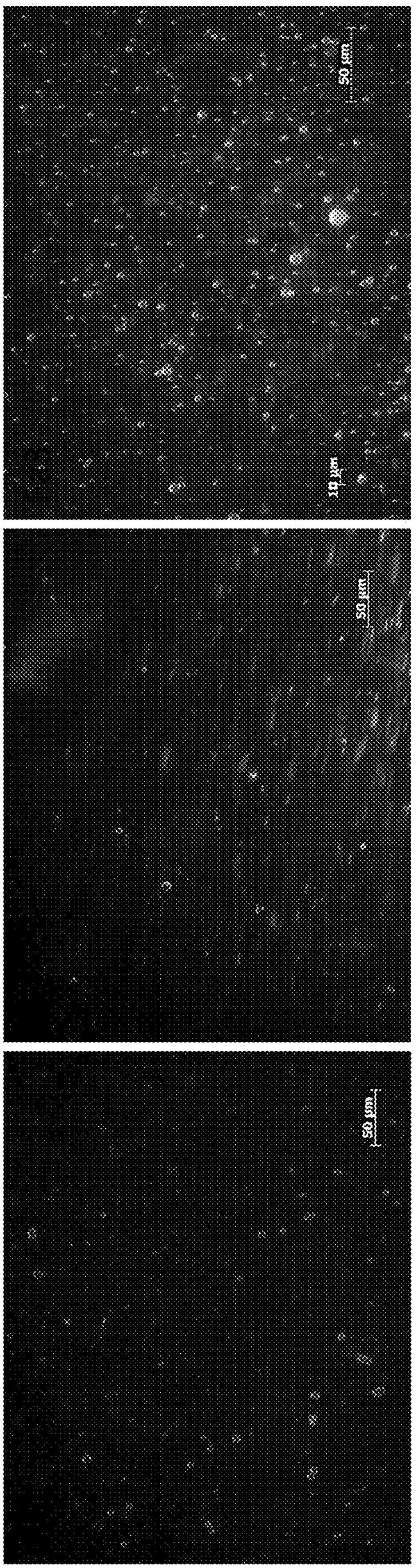
FIG. 1 shows optical microscopic images of preliminary liposomal formulations Fa1, Fa2, and Fa3. Scale bar is 50 μm.

Visual characterization of the liposomal suspensions, Fa1, Fa2, and Fa3, yielded all suspensions with cloudy appearance and having some precipitates (Table 2). The relative abundance of liposomes was qualitatively characterized using light microscopy (FIG. 1) and it was observed that the process of formulating Fa3 generated the highest concentration of liposomes.

TABLE 2

| Visual appearance of preliminary liposomal formulations Fa. | |
|---|---|
| Formulation No. | Observation |
| Fa1 | Cloudy Suspension with precipitate |
| Fa2 | Cloudy Suspension with precipitate |
| Fa3 | Cloudy Suspension with precipitate |

Example 2. Effect of Temperature on Phospholipid Preliminary Liposomes

Figure 2:
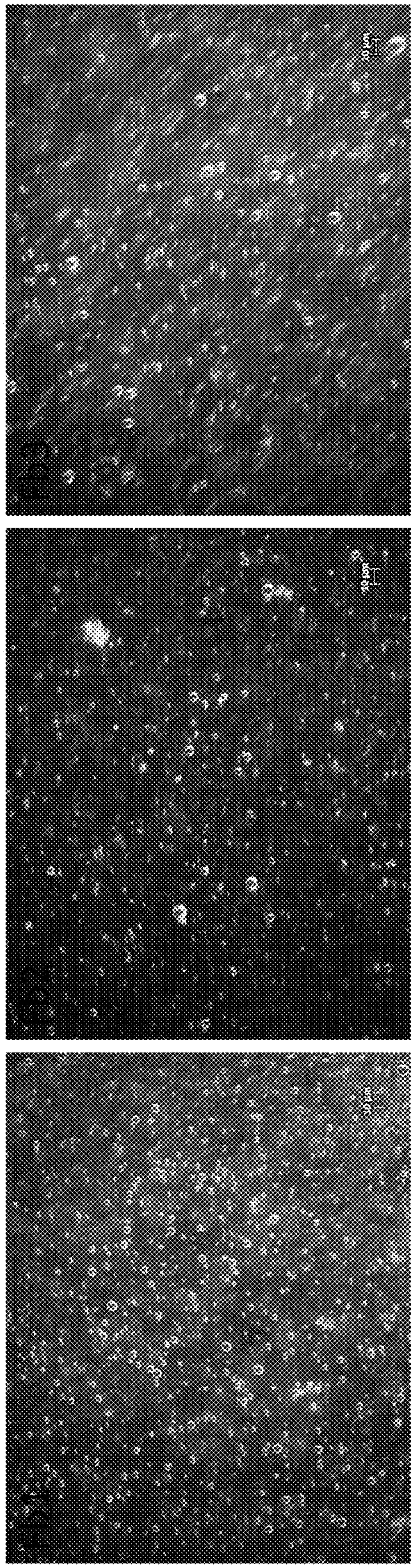
FIG. 2 shows optical microscopic images of preliminary liposomal formulations Fb1, Fb2, and Fb3 that were prepared to assess the effect of temperature on the particle formulation. Scale bar is 10 μm.

To overcome the precipitation observed in the Fa formulations experiments, liposomal suspensions were prepared with differing temperature conditions. The effect of temperature of an aqueous solvent on the dissolution and visual appearance of liposomal suspensions was assessed. Three formulations Fb1, Fb2, and Fb3 were prepared as in Table 3.

deionized water at 20° C. followed by an air injection of DSPC (2 mg/ml), CBD (30 mg/ml) and cholesterol (0.73 mg/ml, 15 molar % of DSPC). The resultant suspension also had a cloud appearance with precipitates of CBD and non-dispersed lipid. Fb3 was prepared using using deionized water at 20° C. followed by an immersed injection of CBD and non-dispersed lipid. Fb3 had a cloudy appearance with observable precipitates of CBD and non-dispersed lipid. (FIG. 2)

TABLE 3

| Water temperature and method of ethanol injection used for Fb formulations. | |
|---|---|
| Formulation No. | Method |
| Fb1 | Water (20° C. ), ethanol (4° C.), immersed injection |
| Fb2 | Air injection, water (20° C.) |
| Fb3 | Immersed injection, water (20° C.) |

Example 3. Effect of CBD Concentration and Method of Preparation

The preparation of lipid nanoparticle formulations (Fc1-Fc9, Table 4) was performed to examine the effect of cannabidiol (CBD) concentration, temperature, and homogenization method on the visual appearance, particle size, and zeta potential of the nanoparticles in suspensions.

TABLE 4

| Formulations c (Fc) of CBD encapsulated in lipid nanoparticles prepared at room temperature (20° C.) or at 60° C. | | |
|---|---|---|
| Formulation No. | Formulation Content | Temperature and Homogenization |
| Fc1 | DSPC (2 mg/ml), CBD (30 mg/ml), Cholesterol (0.73 mg/ml - 15 molar % of DSPC) | Heated (60° C.) |
| Fc2 | DSPC (2 mg/ml), CBD (30 mg/ml), Cholesterol (0.73 mg/ml - 15 molar % of DSPC) | Room Temp (20° C.) |
| Fc3 | DSPC (2 mg/ml), CBD (2 mg/ml), Cholesterol (0.73 mg/ml - 15 molar % of DSPC) | Room Temp (20° C.) |
| Fc4 | DSPC (2 mg/ml), CBD (2 mg/ml), Cholesterol (0.73 mg/ml - 15 molar % of DSPC) | Heated (60° C.) |
| Fc5 | DSPC (2 mg/ml), CBD (2 mg/ml), Cholesterol (0.73 mg/ml - 15 molar % of DSPC) | Homogenized and Room Temp (20° C.) |
| Fc6 | DSPC (2 mg/ml), CBD (2 mg/ml), Cholesterol (0.73 mg/ml - 15 molar % of DSPC) | Heated (60° C.) and Dropwise |
| Fc7 | CBD (2 mg/ml) (control) | Room Temp (20° C.) |
| Fc8 | DSPC (2 mg/ml), CBD (2 mg/ml), Cholesterol (0.73 mg/ml - 15 molar % of DSPC) | Homogenized and Heated (60° C.) |
| Fc9 | DSPC (2 mg/ml), CBD (30 mg/ml), Cholesterol (0.73 mg/ml - 15 molar % of DSPC) | Heated (60° C.) and Dropwise |

Fb1 was prepared in deionized water at room temperature (20° C.) and ethanol at 4° C. The ethanol solution comprising of DSPC (2 mg/ml), CBD (30 mg/ml) and cholesterol (0.73 mg/ml, 15 molar % of DSPC) was introduced into the water using immersed injection technique. The resultant suspension had a cloudy appearance with precipitates of CBD and non-dispersed lipid. Fb2 was prepared using Two concentrations of CBD were used in the formulations, 2 mg/ml and 30 mg/ml, while the concentration of 1,2-distearoyl-sn-glycero-3-phosphocholine (DSPC) was constant for all formulations at 2 mg/ml. Cholesterol concentration was also maintained constant at 0.73 mg/ml (15 mol % of DSPC). Fc1 and Fc4 were formulations that directly compare CBD concentration while the preparation conditions where consistent e.g., temperature and concentrations of DSPC and cholesterol. The effect of the temperature was also assessed. Fc1-Fc4 examined the difference in suspension appearance, precipitates, particle size, and zeta potential at either room temperature (20° C.) or at elevated temperature (60° C.) (Table 5 and FIGS. 3-4). Homogenization of the suspension was performed in formulations Fc5 and Fc8 at either 20° C. (Fc5) or at 60° C. (Fc8). Visual inspection of suspension appearance, precipitates, particle size, and zeta potential at either room temperature (20° C.) or at elevated temperature (60° C.) (Table 5 and FIGS. 3-4). Formulations Fc6 and Fc9 examined the effect of CBD concentration, 2 mg/ml and 30 mg/ml, on the suspension appearance, precipitates, particle size, and nanoparticle zeta potential while the suspension was kept at 60° C. and CBD was added in dropwise manner (Table 5 and FIGS. 3-4). Formulation Fc7 was a control drug-only formulation.

TABLE 5

Visual appearance and the presence of precipitates of formulations Fc1-Fc9.

| Formulation No. | Visual Observations |
|---|---|
| Fc1 | Opaque/cloudy Suspension with precipitate |
| Fc2 | Opaque/cloudy Suspension with precipitate |
| Fc3 | Translucent/milky/less Cloudy Suspension with less precipitate |
| Fc4 | Translucent/milky/less Cloudy Suspension with less precipitate |
| Fc5 | Translucent/milky/less Cloudy Suspension with less precipitate |
| Fc6 | Translucent/milky/less Cloudy Suspension with less precipitate |
| Fc7 | Translucent/less Cloudy Suspension with crystal precipitate |
| Fc8 | Translucent/milky/less Cloudy Suspension with less precipitate |
| Fc9 | Cloudy Suspension with precipitate |

Particle size of formulations Fc1-Fc9 was assessed as mean effective diameter (nm) and mean polydispersity with standard deviation margins (FIG. 3). The smallest size of nanoparticles was observed from formulation Fc1. The method of preparation of formulations Fc1 and Fc4 only differed by the concentration of CBD used. The higher concentration of CBD resulted in larger particles likely due to unentrapped particulates of CBD which is consistent with the largest size of particles observed in formulation Fc7. The method of preparation of formulation Fc1 resulted also in a mixture of smaller lipid nanoparticles and larger unentrapped CBD particulates reflected in the large polydispersity seen in Fc1. Formulation Fc4 showed the optimal method to proceed with given the smallest nanoparticle size and low polydispersity value (FIG. 3).

Zeta potential was also measured for formulations Fc1-Fc9 (FIG. 4). The mean zeta potential in mV was recorded along with the standard deviation (S.D.) from triplicate measurements, where each measurement recorded is an average of 10 runs. The zeta potential value of formulation Fc4 was −0.05 mV with a S.D. of 0.09, consistent with the selection of Fc4 as the optimal formulation because it confirms that CBD was loaded into the nanoparticles and the surface charge of the nanoparticles is near neutral.

Example 4. Effect of Poloxamer on Polymer Particle Composition

The effect of poloxamer concentration on the suspension clarity, amount of precipitate, particle size, suspension pH, and suspension viscosity was examined using PLURONIC® F127 as the poloxamer. Micellar formulations Fd1-Fd6 where prepared using 0.5 g/100 ml CBD and homogenized at the lowest speed of the homogenizer for 2 minutes. PLURONIC® F127 concentration was varied from 1% to 10% w/v from formulations Fd1 to Fd6 respectively as seen in Table 6.

TABLE 6

Formulations of PLURONIC ® F127 micelles with CBD.

| Formulation No. | Formulation Components | Method |
|---|---|---|
| Fd1 | 1% F127 + 0.5% CBD | Homogenisation for 2 minutes (speed: lowest) |
| Fd2 | 2% F127 + 0.5% CBD | Homogenisation for 2 minutes (speed: lowest) |

TABLE 6-continued

Formulations of PLURONIC ® F127 micelles with CBD.

| Formulation No. | Formulation Components | Method |
|---|---|---|
| Fd3 | 3% F127 + 0.5% CBD | Homogenisation for 2 minutes (speed: lowest) |
| Fd4 | 4% F127 + 0.5% CBD | Homogenisation for 2 minutes (speed: lowest) |
| Fd5 | 5% F127 + 0.5% CBD | Homogenisation for 2 minutes (speed: lowest) |
| Fd6 | 10% F127 + 0.5% CBD | Homogenisation for 2 minutes (speed: lowest) |

Formulations Fd1-Fd6 all had a translucent appearance (FIGS. 5-6), as opposed to the cloudy appearance observed in lipid-only nanoparticles. Varying amount of precipitate was observed that correlated with the concentration of PLURONIC® F127 used (Table 7).

TABLE 7

Observed micellar suspension transparency and presence of precipitates.

| Formulation No. | Visual Appearance and Precipitate Observation |
|---|---|
| Fd1 | Translucent, milky suspension, precipitate |
| Fd2 | Translucent, less milky than Fd1 suspension, less precipitate than Fd1 |
| Fd3 | Translucent, less milky than Fd2 suspension, less precipitate than Fd2 |
| Fd4 | Translucent, less milky than Fd3 suspension, less precipitate than Fd3 |
| Fd5 | Translucent, less milky than Fd4 suspension, less precipitate than Fd4 |
| Fd6 | Transparent, minimal precipitate |

Figure 5:
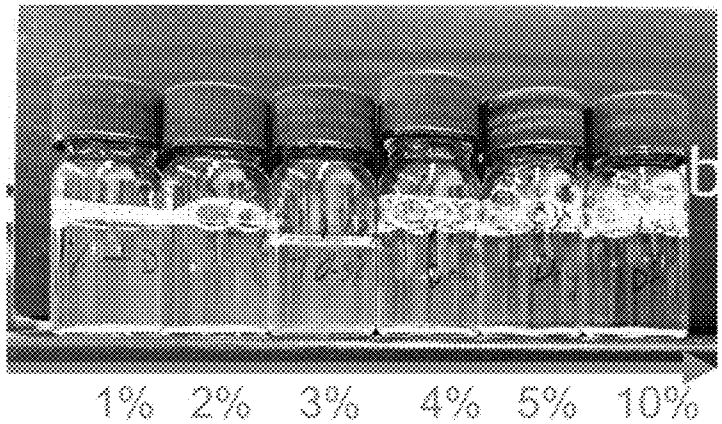
FIG. 5 is a photographic image showing the optical transparency of formulations Fd1-Fd6. The transparency increased with increased concentration of the poloxamer PLURONIC® F127. Concentration of CBD was constant for all suspensions at 0.5% w/w while the PLURONIC® F127 concentration was 1%, 2%, 3%, 4%, 5%, and 10% for formulations Fd1, Fd2, Fd3, Fd4, Fd5, and Fd6 respectively.
Figure 6:
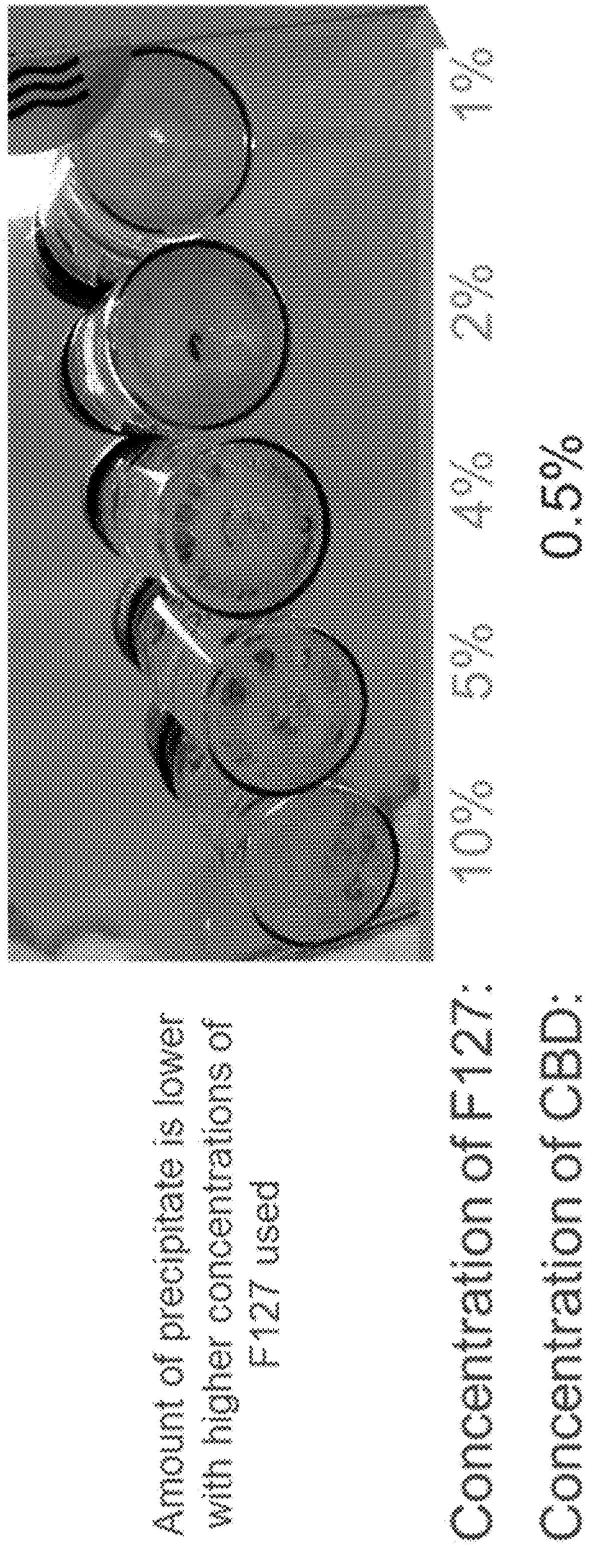
FIG. 6 is a photographic image showing the effect of poloxamer concentration to the amount of observable precipitate in formulations Fd6, Fd5, Fd4, Fd2, and Fd1. Concentration of CBD was constant for all suspensions at 0.5% w/w while the PLURONIC® F127 concentration was 1%, 2%, 4%, 5%, and 10% for formulations Fd1, Fd2, Fd4, Fd5, and Fd6 respectively.
Figure 7:
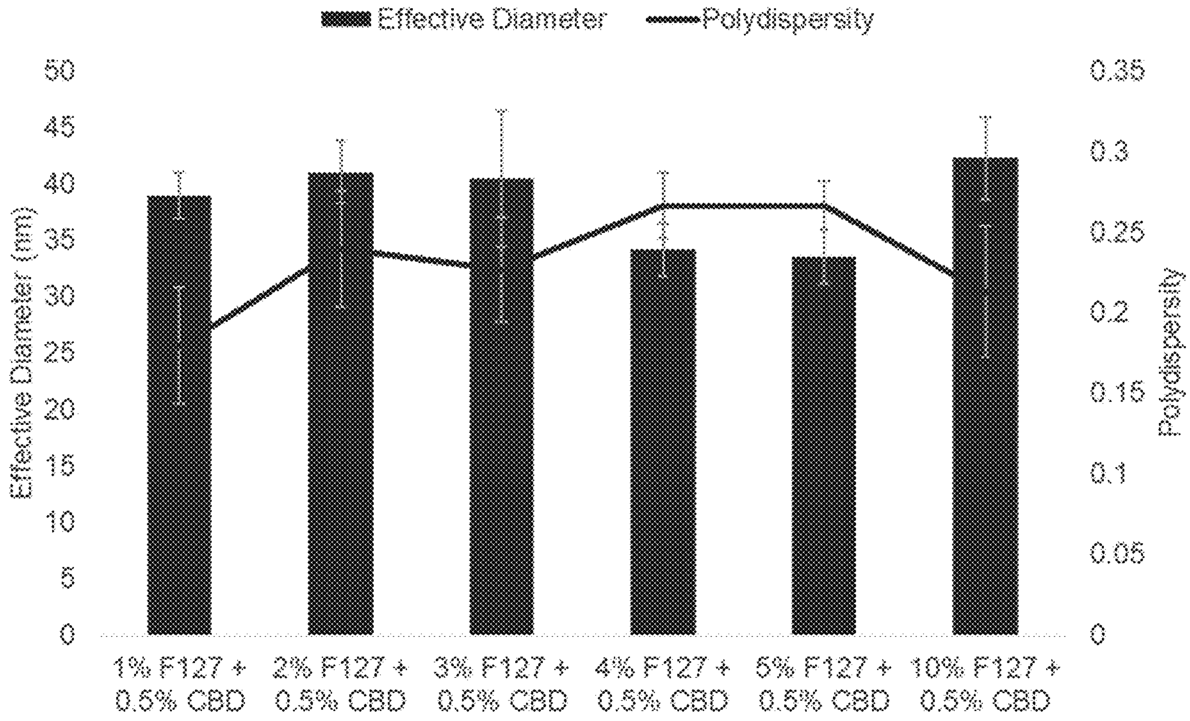
FIG. 7 is graph showing effective diameter and polydispersity of formulations Fd1-Fd6. All formulations resulted in micelles of similar size below 50 μm.
Figure 8:
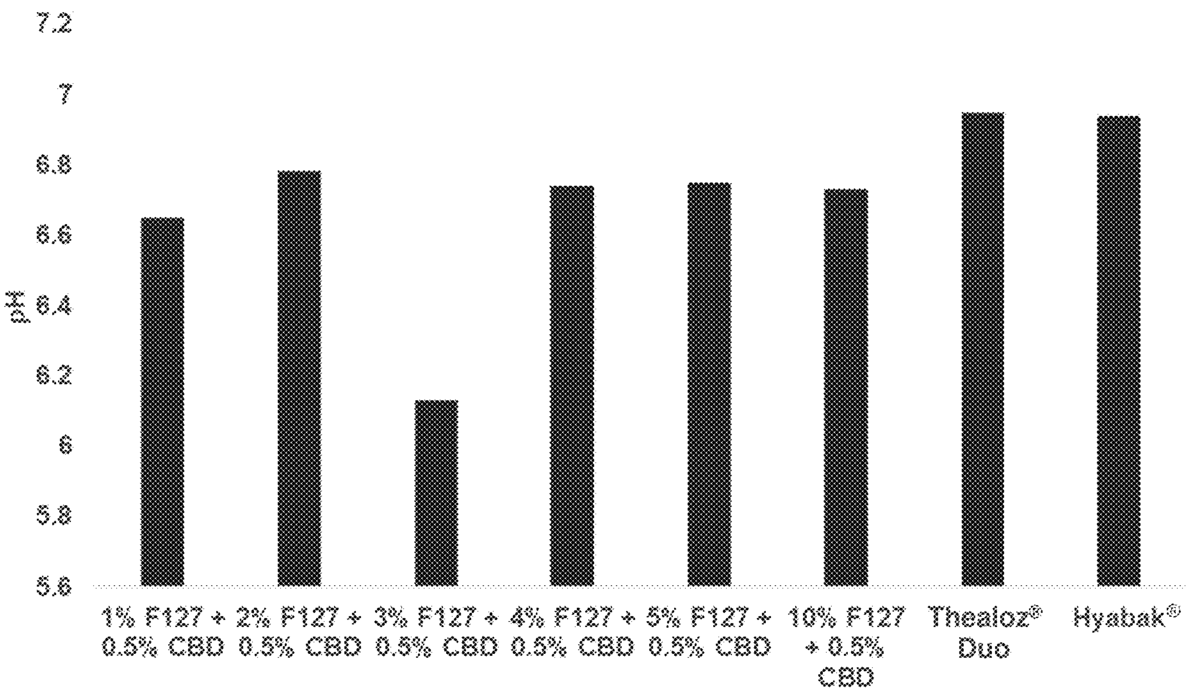
FIG. 8 is graph showing the pH of formulations Fd1-Fd6 in comparison to the pH of commercially available eye drop solutions THEALOZ® DUO and HYABAK®.
Figure 9:
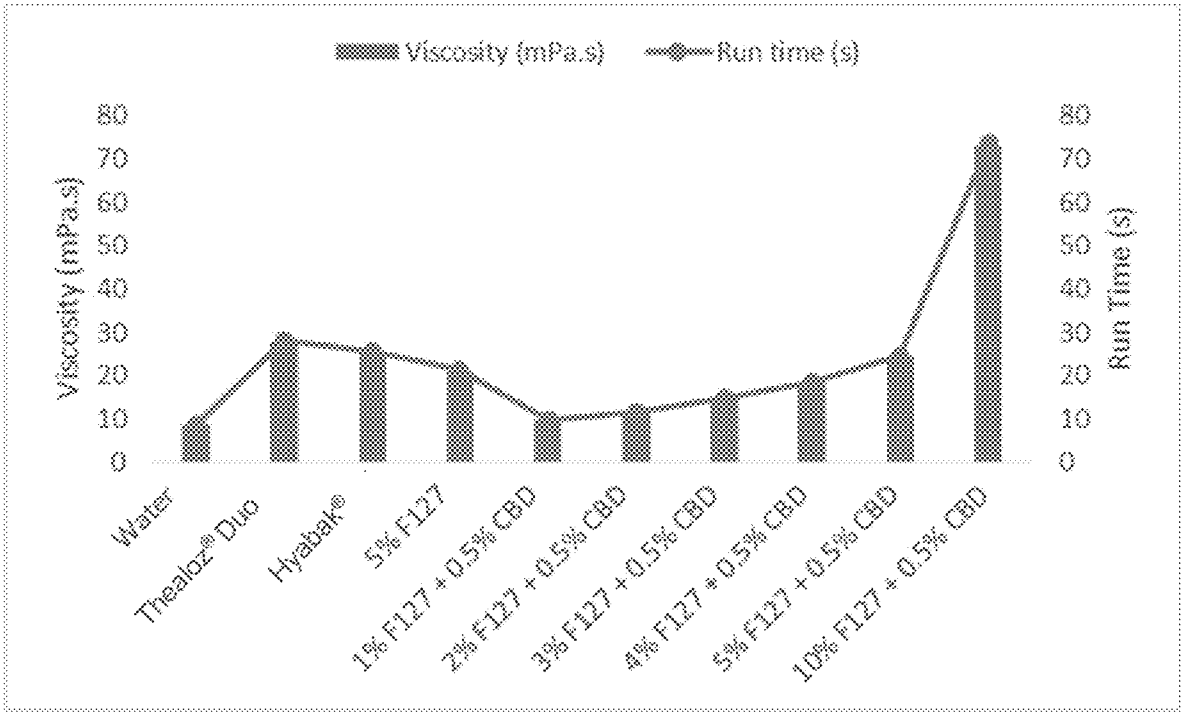
FIG. 9 is graph showing the viscosity of formulations Fd1-Fd6 in comparison the viscosity of water and two commercially available eye drop solutions THEALOZ® DUO and HYABAK®.
Figure 10:
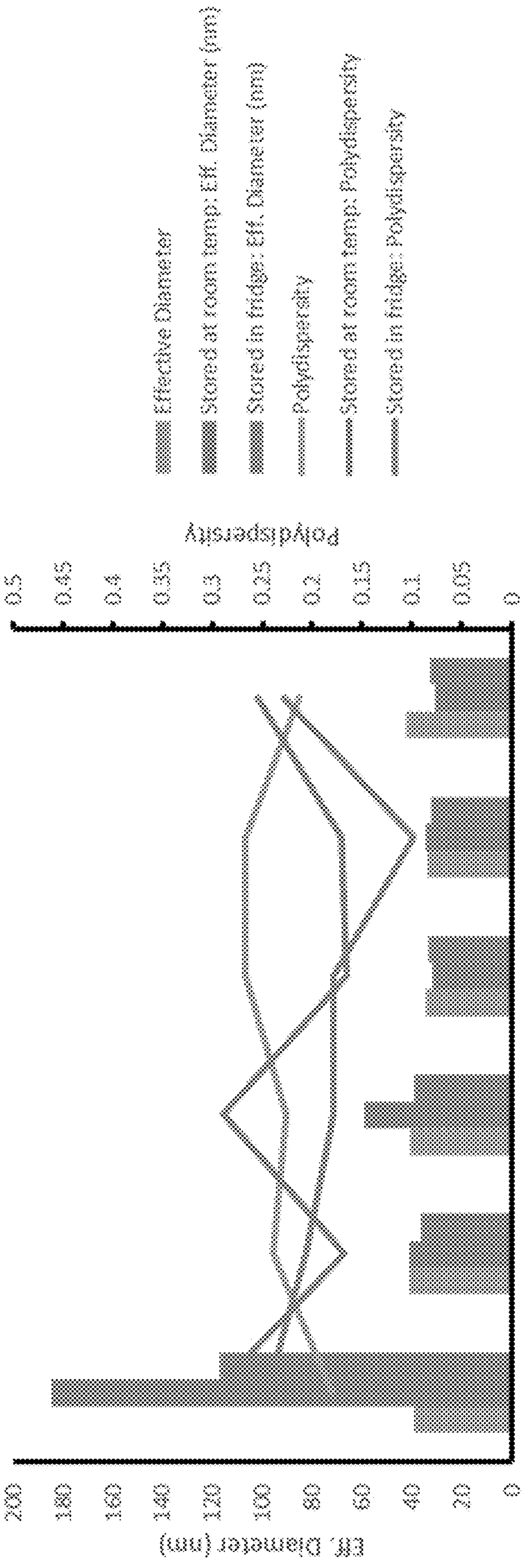
FIG. 10 is graph showing the size stability of formulations Fd1-Fd6. The effective diameter and polydispersity were calculated for all formulations on the day of preparation (bar on the left), and 30 days after preparation when stored in either room temperature 20° C. (bar in the middle) or at 4° C. (bar on the right).

Suspensions with higher PLURONIC® F127 showed higher transparency and also less amount of precipitate indicating the effect of PLURONIC® F127 on the dissolution of CBD (FIGS. 5-6). Particle size was characterized and all formulations resulted in micelles of similar size below 50 nm (FIG. 7). The pH and viscosity of formulations Fd1-Fd6 were measured and compared to two commercially available eye drop solutions, THEALOZ® DUO and HYABAK® (FIGS. 8-9). All PLURONIC® F127 formulations, except for Fd3, had pH values close to neutral pH. Fd3 showed lower pH closer to 6.2 (FIG. 8). Viscosity was also lower than the commercially available eye drop solutions for all but one Fd formulations. Fd10 had a significantly higher viscosity that could be attributed to it being the formulation with the highest CBD concentration (FIG. 9). Stability of Fd1-Fd6 was also characterized on the day of preparation, and after 30 days of storage at either room temperature (20° C.) or at 4° C. (FIG. 10).

Example 5. Formulation of Lipid-Polymer Composite Particles

Figure 11:
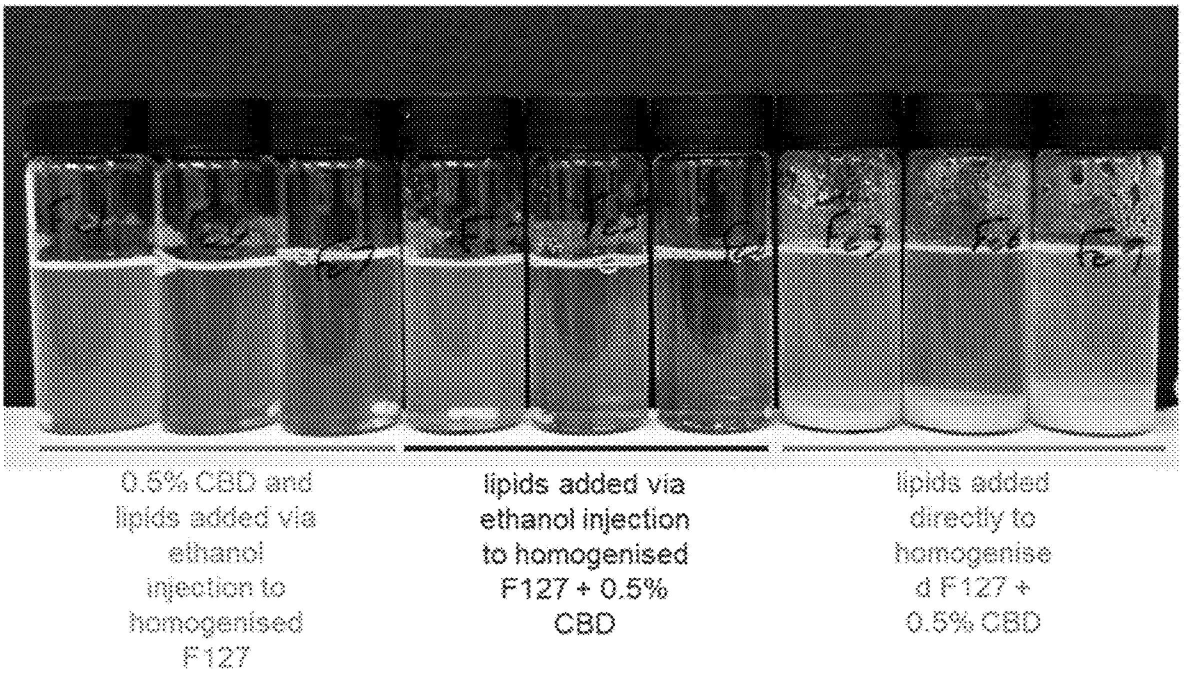
FIG. 11 is a photographic image showing the optical transparency of formulations Fe1-Fe9.

Lipid-polymer composite particles were prepared with PLURONIC® F127 concentrations 1%, 3% and 5% w/v, with 0.5% CBD concentration, with 2 mg/ml 1,2-distearoyl-sn-glycero-3-phosphocholine (DSPC) and 0.73 mg/ml cholesterol into formulations Fe1-Fe9 (Table 8). Characterization of the Fe formulations included visual inspection of transparency and presence of precipitates, particle size and polydispersity, suspension pH, suspension tonicity, size distribution, and size stability after 19 days of storage. Formulations Fe1, Fe4 and Fe7 where homogenized with all of the components at 60° C. with DSPC and cholesterol added to the suspension mixture via ethanol injection. Formulations Fe2, Fe5, and Fe8 were prepared in two steps. First, PLURONIC® F127 was homogenized with CBD followed by addition of DSPC and cholesterol via ethanol injection. Formulations Fe3, Fe6 and Fe9 were also prepared in two separate steps. First, PLURONIC® F127 was homogenized with CBD. Then a powder mixture of DSPC and cholesterol was added directly to the PLURONIC® F127-CBD suspension at 60° C. Upon visual inspection all suspensions were translucent (Table 9 and FIG. 11). Formulations Fe1, Fe4, and Fe7 had a milky appearance with less milky appearance with increased PLURONIC® F127

TABLE 8

Formulation of lipid-polymer composite particles.

| Formulation No. | Formulation Components and Method of Preparation |
|---|---|
| Fe1 | Homogenised 1% F127. 0.5% CBD and lipids (2 mg/ml DSPC and 0.73 mg/ml cholesterol) added via ethanol injection at 60° C. |
| Fe4 | Homogenised 3% F127. 0.5% CBD and lipids (2 mg/ml DSPC and 0.73 mg/ml cholesterol) added via ethanol injection at 60° C. |
| Fe7 | Homogenised 5% F127. 0.5% CBD and lipids (2 mg/ml DSPC and 0.73 mg/ml cholesterol) added via ethanol injection at 60° C. |
| Fe2 | Homogenised 1% F127 + 0.5% CBD. Lipids (2 mg/ml DSPC and 0.73 mg/ml cholesterol) added via ethanol injection at 60° C. |

TABLE 8-continued

| Formulation of lipid-polymer composite particles. | |
|---|---|
| Formulation No. | Formulation Components and Method of Preparation |
| Fe5 | Homogenised 3% F127 + 0.5% CBD. Lipids (2 mg/ml DSPC and 0.73 mg/ml cholesterol) added via ethanol injection at 60° C. |
| Fe8 | Homogenised 5% F127 + 0.5% CBD. Lipids (2 mg/ml DSPC and 0.73 mg/ml cholesterol) added via ethanol injection at 60° C. |
| Fe3 | Homogenised 1% F127 + 0.5% CBD. Lipids (2 mg/ml DSPC and 0.73 mg/ml cholesterol) powder added directly at 60° C. |
| Fe6 | Homogenised 3% F127 + 0.5% CBD. Lipids (2 mg/ml DSPC and 0.73 mg/ml cholesterol) powder added directly at 60° C. |
| Fe9 | Homogenised 5% F127 + 0.5% CBD. Lipids (2 mg/ml DSPC and 0.73 mg/ml cholesterol) powder added directly at 60° C. |

concentration. Formulations Fe2, and Fe5 also showed decreased precipitates and milky appearance with increased PLURONIC® F127 concentration. Fe8 appeared transparent and had no observable precipitates (Table 9 and FIG. 11). Formulations Fe3, Fe6, and Fe9 also had a milky appearance (FIG. 11) with a soft/cloudy precipitate observed in Fe6, and Fe9.

TABLE 9

| Observed Fe formulation transparency and presence of precipitates. | |
|---|---|
| Formulation No. | Formulation Components and Method of Preparation |
| Fe1 | Translucent, milky suspension with precipitate (less than Fe3, Fe6 and Fe9) |
| Fe4 | Translucent, less milky than Fe1 suspension with precipitate (less than Fe3, Fe6 and Fe9) |
| Fe7 | Translucent, less milky than Fe4 suspension with precipitate (less than Fe3, Fe6 and Fe9) |
| Fe2 | Translucent and milky with precipitate |
| Fe5 | Translucent and milky, no precipitate |
| Fe8 | Transparent, no precipitate |
| Fe3 | Translucent, milky suspension with precipitate |
| Fe6 | Translucent, less milky than Fe3 suspension with soft/cloudy precipitate |
| Fe9 | Translucent, less milky than Fe6 suspension with soft/cloudy precipitate |

In formulations Fe1, Fe4, and Fe7 the particle size and polydispersity decreased with increased PLURONIC® concentration. This trend was also observed in formulations Fe2, Fe5, and Fe8. In formulations Fe3, Fe6, and Fe9 the concentration of PLURONIC® did not correlate with the particle size. This was potentially due to the reduced dissolution of DSPC and cholesterol via the direct addition of these in powder form (FIG. 12). Particle span values for all formulations ranged between approximately 1.00 to 1.60 (FIG. 12) while polydispersity was lowest for particles in formulation Fe5. In general, formulations Fe2, Fe5, and Fe8 had the lowest mean particle size. pH across all formulations was close to neutral pH (FIG. 13). Tonicity of the formulations was also measured and compared to saline control solution, suspensions of PLURONIC® F127 and CBD only, and with commercially available eye drop solutions HYABAK® 0.15%, and THEALOZ® DUO (FIG. 14). Size distribution was characterized for all formulations showing two particle size populations. Formulations Fe5 and Fe8 showed a decreased abundance of the population of particles of larger size compared to the population of particles of lower size. Stability of Fe1-Fe6 was also characterized on the day of preparation, and after 19 days of storage at either room temperature (20° C.) or at 4° C. (FIG. 15). All formulations showed stable size stability at 19 days in either room temperature (20° C.) or at 4° C. except for Fe1 and Fe9. Visual inspection of all formulation was performed at 19 days from preparation with minimal to moderate color change to an orange/pink hue for all the formulations store at room temperature. Formulations stored at 4° C. did not have observable color or appearance changes from the day of preparation (Table 10).

TABLE 10

| Color change in formulations Fe. | |
|---|---|
| Formulation No. | Observation after 19 days from preparation stored at 20° C. |
| Fe1 | minimal color change to orange/pink |
| Fe4 | minimal color change to orange/pink |
| Fe7 | minimal color change to orange/pink |
| Fe2 | color change to orange/pink |
| Fe5 | color change to orange/pink |
| Fe8 | color change to orange/pink |
| Fe3 | color change to orange/pink |
| Fe6 | color change to orange/pink |
| Fe9 | color change to orange/pink |

Example 6. Method Optimization of Chosen Formulations

A selection of formulations was further optimized (Table 11). Duplicates of each formulation Fd5, Fe5, Fe8, and Fe2 were prepared and the particle size and polydispersity were characterized (FIG. 16). Formulations Fd5, Fe5, and Fe8 yielded optimal particle size and polydispersity.

TABLE 11

| Lipid-polymer composite particle optimization formulations. | | |
|---|---|---|
| Formulation No. | Formulation | Method |
| Fd5 | F127 5% + 0.5% CBD | Homogenise for 2 min |
| Fd5 | F127 5% + 0.5% CBD | Homogenise for 2 min |
| Fe5 | F127 3% + 0.5% CBD + Lipids | Homogenise for 2 min, ethanol injection 7 sec/750 µl at 60° C., evaporate 2 h |
| Fe5 | F127 3% + 0.5% CBD + Lipids | Homogenise for 2 min, ethanol injection 7 sec/750 µl at 60° C., evaporate 2 h |
| Fe8 | F127 5% + 0.5% CBD + Lipids | Homogenise for 2 min, ethanol injection 7 sec/750 µl at 60° C., evaporate 2 h |
| Fe8 | F127 5% + 0.5% CBD + Lipids | Homogenise for 2 min, ethanol injection 7 sec/750 µl at 60° C., evaporate 2 h, homogenise for 2 min |
| Fe2 | F127 1% + 0.5% CBD + Lipids | Homogenise for 2 min, ethanol injection 7 sec/750 µl at 60° C., evaporate 2 h, homogenise for 2 min |
| Fe2 | F127 1% + 0.5% CBD + Lipids | Homogenise for 2 min, ethanol injection 7 sec/750 µl at 60° C., evaporate 2 h, homogenise for 2 min |

Example 7. Effect of PLURONIC® F127 and Lipid Concentration on the Solubility of CBD CBD has a very low solubility in water and a high lipophilicity, rendering it a class 2 classification by the Biopharmaceutical Classification System (BCS). Such low water solubility presents a challenge for bioavailability of CBD during pharmaceutical administration. For a fasting individual the oral bioavailability of CBD is only around 6%. The aim of this study was to investigate the effect on the solubility of CBD in the presence of increasing concentrations of PLURONIC® F127 as well as increasing concentration of the lipids DSPC and cholesterol along with combinations of PLURONIC® F127, DSPC, and cholesterol.

PLURONIC® F127, 18:0 DSPC (1,2-distearoyl-sn-glycero-3-phosphocholine) and cholesterol (sheep wool) was obtained from Sigma Aldrich. Cannabidiol (CBD) was provided by MaxBiotech. Formulations containing PLURONIC® F127 at concentrations of 1, 3, 5, 7, 9, 11, 13 and 15% w/v were prepared by dissolving PLURONIC® F127 in distilled water. To prepare the PLURONIC® F127 formulations at these concentrations the formulations were stirred on a heated magnetic stirrer at 34° C. Stock formulations of lipids for ethanol injection were prepared using DSPC in ethanol at concentrations of 2, 4, 8 and 16 mg/ml and cholesterol in ethanol at concentrations of 0.73, 1.46, 2.92 and 5.84 mg/ml.

Methods

Saturated Solubility of CBD

To determine the saturated solubility of CBD in the presence of PLURONIC® F127, PLURONIC® formulations were made as above. To each formulation excess CBD was added and left stirring overnight on a magnetic stirrer at room temperature (FIG. 17). To see how addition of lipids affects saturated solubility, lipids were added to 5% PLURONIC® F127 containing excess CBD using the ethanol injection method. For this, a 19G needle was immersed into the formulation being stirred, and 8.11% (volume of sample end volume) of the lipid stock formulation was injected at the rate of 750 µl/7 sec. Each formulation at this point was then left stirring overnight as above. On the following day, the formulations were filtered using 0.45 µm syringe filters and the amount of CBD dissolved was quantified using high pressure liquid chromatography.

Determining Effect of Increasing Lipid Concentrations

A volume of 20 ml (v1) was used as the target end volume while investigating the effect of lipids in the system. Two methods were used to investigate the effect of increasing lipid concentration on the micellar system. In the first, CBD was added before ethanol injection while in the second CBD was added after ethanol injection and after the evaporation of ethanol from the system.

Different lipid stocks were prepared as above in ethanol. Excess CBD was added to 20 ml (v1) of 5% PLURONIC® F127 and stirred on a magnetic stirrer and the formulation was brought to a temperature from 45-60° C. While still stirring on the hot plate, lipids were added into the PLURONIC® formulations using the ethanol injection method. A 19G needle was immersed into the formulation being stirred, and 1.62 ml (8.11% v/v (v2)) of the lipid stock formulation was injected at the rate of around 750 µl/7 sec. Here $v2=(v1/100)\times 8.11$. To evaporate the ethanol, the formulations were left uncovered, stirring on the hot plate for 2 hours at 45° C. and after that stirring overnight uncovered at room temperature.

The other method to check for the impact of incorporating higher concentrations of lipids, CBD was incorporated after ethanol injection. This method was similar to the method described in the previous section, with the difference being that the ethanol injection to incorporate lipids was done before addition of CBD. After ethanol injection, the formulations were left uncovered to stir at 45° C. for 2 hours and then at room temperature overnight to evaporate the ethanol. Next day excess CBD was added to the formulations and stirred.

CBD content was determined by diluting the samples in acetonitrile (ACN) (as needed) and then analysing them using HPLC. Calibration curve and sample quantification was carried out using an Agilent Infinity 1260 system. An Eclipse Plus C18, 4.6×150 mm, 3.5 µm column was purchased from Phenomenex. The mobile phase used was ACN:Water (82:18 v/v). HPLC analysis was carried at room temperature at a flow rate of 1 ml/min and an injection volume of 20 µl. The UV detector for HPLC analysis was set at 220 nm. Particle size and polydispersity was determined using a Brookhaven dynamic light scattering system.

Results

PLURONIC® F127 was able to substantially increase the solubility of CBD in water which will increase the permeability and therefore the bioavailability of orally administered CBD. Peak CBD concentrations of approximately 2% w/v in formulations containing PLURONIC® F127 from 7% to 11% (FIG. 18) were observed. Upon visual characterization, using TEM, of the particles produced in the formulations closely packed micelles ranging in size from 20-30 μm in suspensions of 5% PLURONIC® F127 were observed (FIG. 19). In suspensions containing lipids only (DSPC:Chol; (0.21:0.19Mm)) the presence of two distinct types of structures, small and diffuse spherical structures and large clumped structures was observed (FIG. 19). In suspensions of 5% PLURONIC® F127 +DSPC:Chol (0.21:0.19 mM)) two distinct features, closely packed structures were observed having a particle size of 20-30 μm and unilamellar and multilamellar structure with smaller micelles encapsulated within them.

Characterization of Formulations with CBD Added Before Ethanol Injection

Formulations with CBD added before ethanol injection were characterized. The visual appearance of the formulations was recorded (Table 12). Three formulations containing increasing lipid concentrations in waters, in the absence of PLURONIC® F127, and with CBD added before ethanol injection, showed a cloudy appearance.

TABLE 12

Visual appearance of formulations with CBD added before ethanol injection

| Formulation | Observation (after filtration) |
|---|---|
| DSPC:Chol 0.41:0.38 mM (water) | Slightly cloudy |
| DSPC:Chol 0.82:0.76 mM (water) | More cloudy than above |
| DSPC:Chol 1.64:1.51 mM (water) | More cloudy than above |
| DSPC:Chol 0.41:0.38 mM (5% F127) | Cloudy, precipitate (after overnight rest), pink tint |
| DSPC:Chol 0.82:0.76 mM (5% F127) | More cloudy than above, precipitate (after overnight rest), pink tint |
| DSPC:Chol 1.64:1.51 mM (5% F127) | More cloudy than above, precipitate (after overnight rest), pink tint |

When PLURONIC® F127 was included in the formulations at 5% w/v, the appearance of all three different formulations (Table 12) was cloudy, with observable precipitates, and with a pink tint. The particle size and polydispersity of the formulations (FIG. 20) were also characterized. Particle size was higher without PLURONIC® F127, and in the formulations containing PLURONIC® F127, the particle size increased with increasing lipid concentration (FIG. 20). The pH of the formulations was also measured with no substantial differences in pH in the presence or absence of PLURONIC® F127 (FIG. 21).

The amount of CBD dissolved in the formulations with PLURONIC® F127 and without PLURONIC® F127 was characterized (FIG. 22). There was a significant difference in the amount of CBD dissolved when PLURONIC® F127 was included in the formulations. The concentration of lipids in the formulations did not show an effect in the amount of CBD solubility purely aqueous solutions (FIG. 22).

Characterization of Formulations with CBD Added After Ethanol Injection

Formulations with CBD added after ethanol injection. The visual appearance of the formulations was recorded (Table 13). Three formulations containing increasing lipid concentrations in waters, in the absence of PLURONIC® F127, and with CBD added before ethanol injection, showed a cloudy appearance.

TABLE 13

Visual appearance of formulations with CBD added after ethanol injection

| Formulation | Observation (after filtration) |
|---|---|
| DSPC:Chol 0.41:0.38 mM (water) | Slightly cloudy |
| DSPC:Chol 0.82:0.76 mM (water) | More cloudy than above |
| DSPC:Chol 1.64:1.51 mM (water) | More cloudy than above |
| DSPC:Chol 0.41:0.38 mM (5% F127) | Cloudy, precipitate (after overnight rest) |
| DSPC:Chol 0.82:0.76 mM (5% F127) | More cloudy than above, precipitate (after overnight rest) |
| DSPC:Chol 1.64:1.51 mM (5% F127) | More cloudy than above, precipitate (after overnight rest) |

When PLURONIC® F127 was included in the formulations, at 5% w/v, the appearance of all three different formulations (Table 13) was cloudy, with observable precipitates, but without the pink tint observed when the ethanol injection was performed after CBD addition. The particle size and polydispersity of the formulations (FIG. 23) was also characterized. Particle size was higher without PLURONIC® F127, and in the formulations containing PLURONIC® F127, the particle size increased with increasing lipid concentration (FIG. 23). The pH of the formulations was also measured with no substantial differences in pH in the presence or absence of PLURONIC® F127 (FIG. 24).

The amount of CBD dissolved in the formulations with PLURONIC® F127 and without PLURONIC® F127 was characterized (FIG. 25). There was a significant difference in the amount of CBD dissolved when PLURONIC® F127 was included in the formulations. The concentration of lipids in the formulations did not show an effect in the amount of CBD solubility purely aqueous solutions (FIG. 25).

DISCUSSION

As presented in this experiment, PLURONIC® F127 was able to substantially increase the solubility of CBD in water. TEM images show that incorporating lipids into the PLURONIC® formulations containing CBD results in unilamellar and multilamellar liposomes, which seemingly contained micelles within them. These hybrid systems will translate to enhanced absorption of orally administered CBD. Although increasing lipid concentration may have resulted in increased concentration of these multi-particulate systems there is a modest enhancement in CBD solubility compared to PLURONIC® on its own. However, the hybrid particles containing lipid coated micelles may act by shielding micelles within and thus keeping micellar integrity when the formulation is diluted, as may be the case upon administration. Another interesting observation with DSPC:Chol concentrations of 1:64:1.51 was that substantially bigger (double in size) particles were formed with the method in which ethanol injection is done after incorporation of CBD into the system. This may mean that this order of CBD incorporation and ethanol injection leads to more micellar entrapment within the liposomes and or more drug entrapment within the hybrid composite particles.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. Other embodiments are within the claims.

The invention claimed is:

1. A method of preparing a composition comprising a plurality of lipid-polymer composite particles encapsulating a bioactive agent, the method comprising:

(a) homogenizing the bioactive agent with a poloxamer to produce a homogenized solution; and following step (a)

(b) injecting a sterol and a lipid selected from the group consisting of a neutral lipid, a cationic lipid, and an anionic lipid, and a sterol, into the homogenized solution;

thereby producing the plurality of lipid-polymer composite particles encapsulating the bioactive agent, wherein the plurality of lipid-polymer composite particles comprise unilamellar or multilamellar structures encapsulating one or more micelles, wherein the plurality of lipid-polymer composite particles has a mean particle size of between 10 and 1000 nanometers, and wherein the composition lacks an organic solvent to solubilize the active agent.

2. The method of claim 1, wherein the bioactive agent is a therapeutic agent, a nutraceutical agent, or a recreational agent.

3. The method of claim 1, wherein the bioactive agent is a cannabinoid, a terpene, a flavonoid, an antibiotic, an antiseptic agent, an antifungal, an antibacterial, an analgesic, an anti-inflammatory agent, an antiprotozoal agent, a steroid, an antiviral agent, a lipophilic drug, an anti-VEGF agent, an anti-glaucoma agent, an immunogen, nicotine, cyclosporin A, tacrolimus, isotretinoin, propofol, griseofulvin or any combination thereof.

4. The method of claim 1, wherein the weight ratio of the poloxamer and the bioactive agent is between 2 and 15.

5. The method of claim 1, wherein the lipid comprises of a carbon chain of length from 4 to 22 and a neutral, cationic, or anionic head group.

6. The method of claim 1, wherein the lipid is a phosphatidylcholine, a phosphatidylserine, a phosphatidylglycerol, a phosphatidylethanolamine, or a phosphatidylinositol.

7. The method of claim 1, wherein the concentration of the lipid is from about 0.1 mol % to about 10 mol %.

8. The method of claim 1, wherein the sterol is a phytosterol, cholesterol, or a cholesterol analog selected from thiocholesterol, epicholesterol, β-sitosterol, stigmasterol, and lanosterol.

9. The method of claim 1, wherein the concentration of the sterol is from about 5 mol % to about 50 mol % of the total lipid composition.

10. The method of claim 1, wherein the weight ratio of the sterol to the lipid is from about 0.01 to about 0.50.

11. The method of claim 1, wherein step (b) comprises immersed injection of the sterol and the lipid.

12. The method of claim 11, wherein step (b) comprises immersed ethanol injection of the sterol and the lipid.

13. The method of claim 1, wherein step (a) is performed at 50° C. to 70° C.

14. A composition comprising a plurality of lipid-composite particles produced by the method of claim 1.

* * * * *